United States Patent
Bakaltcheva et al.

(10) Patent No.: US 7,931,919 B2
(45) Date of Patent: Apr. 26, 2011

(54) METHOD OF PRODUCING GLYCINE-STABILIZED, LYOPHILIZED PLASMA

(75) Inventors: Irina B. Bakaltcheva, Springfield, VA (US); Lloyd Ketchum, Duluth, MN (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1169 days.

(21) Appl. No.: 11/503,373

(22) Filed: Aug. 14, 2006

(65) Prior Publication Data

US 2010/0273141 A1    Oct. 28, 2010

Related U.S. Application Data

(60) Provisional application No. 60/707,526, filed on Aug. 12, 2005.

(51) Int. Cl.
*A61K 35/16* (2006.01)
(52) U.S. Cl. ...................................... 424/530
(58) Field of Classification Search .................. None
See application file for complete search history.

(56) References Cited

U.S. PATENT DOCUMENTS 4,579,735 A * 4/1986 Heimburger et al. ......... 424/530

OTHER PUBLICATIONS

Hellstern et al., "Manufacture and in vitro characterization of a solvent/detergent-treated human plasma", Vox Sanguinis 63 (3) : 178-185 (1992).*

* cited by examiner

*Primary Examiner* — Sandra Saucier
(74) *Attorney, Agent, or Firm* — Elizabeth Arwine

(57) ABSTRACT

The invention is directed to stabilized whole-cell plasma, which retains the integrity and overall stability of the proteins and other macromolecules of the plasma. Stabilization is accomplished by the addition of glycine to plasma which allows for stabilization prior to freeze drying. Glycine, in the presence of the salt concentration in the plasma, does not recrystallize and acts as a superior stabilizer for the lyophilized plasma. The stability of the freeze dried plasma may be further improved by addition of protectants including calcium chloride, trisodium citrate, hydroxyethyl starch, ammonium sulfate and citric acid to maintain physiologic pH. Superior stability for a wide variety of plasma proteins and functions is shown. A system for the large scale preparation of sterile lyophilized plasma is also provided.

3 Claims, 13 Drawing Sheets

METHOD OF PRODUCING GLYCINE-STABILIZED, LYOPHILIZED PLASMA

REFERENCE TO RELATED APPLICATIONS

This application claims priority to U.S. Provisional Application No. 60/707,526 entitled "Glycine Stabilized Lyophilized Plasma and Method for Making Same" filed Aug. 12, 2005, the entirety of which is hereby incorporated by reference.

RIGHTS IN THE INVENTION

This invention was made with support from the United States Government, Department of the Army, and, accordingly, the United States has certain rights in the invention.

BACKGROUND OF THE INVENTION

1. Field of the Invention

The instant invention relates to lyophilized whole plasma and/or components thereof, and more specifically, to lyophilized whole plasma and/or components thereof that are stabilized by glycine, and which can be reconstituted with water to thereby exhibit physiological characteristics of control or untreated plasma.

2. Description of the Background

Whole plasma and fresh frozen plasma (FFP) are the primary preparation forms for plasma storage. In locales where it can be problematic to readily obtain whole plasma, such as, for example, forward positions of a battlefield, FFP is the preferred storage form. While the use of FFP is preferred in such environs, there remain several limitations. For example, the use of FFP can be limited by the facilities required to transport, store and maintain FFP at temperatures of −25° C. or below. Also, because FFP is often transported/stored using dry ice, it can be difficult to transport FFP given the hazards associated with the use of dry ice, i.e., an transport, and/or the amount of FFP that can be shipped is often limited. Finally, because FFP is frozen, it can take time to properly thaw FFP prior to being used.

Clearly, then, the physical and logistical limitations associated with FFP negatively effects the forward availability of plasma.

Accordingly, the ability to freeze dry plasma would effectively remedy the storage and shipment problems associated with the use of FFP- by converting liquid plasma into a solid, lightweight, stable at ambient temperature, product. While lyophilization of plasma would certainly be advantageous on the battlefield, it would also be beneficial to, for example, developing countries where facilities for preparation, transportation and storage of frozen blood products may be limited.

Pooled plasma was lyophilized for the first time during World War II. However, it was discovered that the process of lyophilization did not kill viruses in plasma. In addition, the use of plasma from large pools carried an unacceptable risk of transmitting pathogens. Therefore, the production of a stable lyophilized plasma product was abandoned.

In recent years several methods for pathogen inactivation in plasma have been introduced. Such methods are typically based on: solvent/detergent treatment; utilization of vitamin B2, Riboflavin, and light, and the application of psoralens and UV light. The current endeavor is to lyophilize pathogen inactivated plasma products. These products will guarantee both unconstrained plasma availability and safety.

Several groups have reported stability results for lyophilized pathogen inactivated solvent/detergent (SD) treated plasma products. Hellstern et al. (Vox Sang; 63: 178-185 (1992)), describe the production of lyophilized and deep-frozen batches of human SD plasma and the in vitro characterization of the product. Clotting factor activities were found to decrease more markedly in the lyophilized plasmas than in the deep frozen batches, Storage stability data at ambient temperature are not reported in this study. The German Red Cross introduced a lyophilized pathogen inactivated SD plasma product in 1990. The product was examined to determine whether the quality is comparable to standard preparations. Several publications report these results. It was found, however, that lyophilized SD plasma did not fulfill basic requirements. The time required to reconstitute the lyophilized product was too long. The resultant pH values were close to alkaline range, and thus unsuitable for use without considerable changes in blood gas and electrolyte levels could be expected in the recipient. In a separate study, the quality of three conventional fresh-frozen plasma preparations and one lyophilized SD plasma preparation were compared. Coagulation activity was significantly reduced in the lyophilized SD plasma. Storage stability data at ambient temperature is not reported in these studies. In Thailand, lyophilized plasma has been used as an in home treatment of hemophilia patients since 1982. The chemical and coagulation properties of this product are nearly the same as FFP after reconstitution with sterile water. The clinical effectiveness of this product has been shown in hemophiliac patients with bleeding episodes. However, storage of the freeze-dried plasma product is still confined to 4° C.

Proteins are relatively unstable molecules and require protectants to improve their stability upon lyophilization and storage. Common compounds used for that purpose are the "polyols", such as sugars, and various hypotheses are being proposed to explain their stabilizing effect on solid proteins. The two disaccharides sucrose and trehalose are among the most commonly used protein stabilizers in lyophilized formulations. Their protective properties are well documented, including their ability to protect coagulation factor proteins and fibrinogen. A lyophilized recombinant factor IX formulation is developed, which contains 1% sucrose as a protectant. Sucrose is used to develop stable albumin-free lyophilized formulations of recombinant factor VIII-SQ (r-VIII SQ) and recombinant factor VIII (BDDrF VIII). Sucrose, trehalose, raffinose and arginine are listed as stabilizing agents in the albumin-free factor VIII formulations designed by Besman et al. (U.S. Pat. No. 6,586,573). Sucrose is also the protein stabilizer of choice used in formulating lyophilized hemostatic fibrinogen/thrombin sandwich bandages stable at ambient temperature.

Bulking agents are used in protein formulations to provide the lyophilized cake a pharmaceutically elegant (i.e., noncollapsed) structure or to support potent biopharmaceuticals used at low doses (mass) per vial. However, under specific conditions bulking agents may display a stabilizing effect as well. Whole plasma does not require a bulking agent to support the structure of the lyophilized cake and is often lyophilized without addition of any excipients.

Glycine is non-toxic, highly soluble, and has a high eutectic temperature when it crystallizes from frozen solution. The latter promotes efficient freeze-drying. The ability of a solute to function as a cryoprotectant or lyoprotectant, however, requires that the compound remain amorphous. The fact that glycine is a crystallizing agent disqualifies it as a protectant.

As crystallizing agents crystallize they separate from the protein phase thus leaving the protein without protection.

Amino acids are often included in protein formulations. L-arginine, L-isoleucine, and L-glutamic acid are used as a mixture to stabilize recombinant factor VIII in lyophilized form. Bush et al. (Seinin Hematol., 35 (2 Suppl 2): 18-21 (1998)) have developed a formulation for recombinant factor IX, which contains 10 mM histidine, 0.26 mM glycine, 1% sucrose, and 0.005% polysorbate-80. According to the authors, polysorbate 80 and sucrose protect the protein from freezing- and freeze-drying induced damage, respectively. Histidine provides buffering stability. Glycine serves as a bulking agent, providing high-quality cake morphology. A sucrose/glycine formulation is utilized for factor VIII lyophilization as well.

Glucose/dextrose also poses a challenge for lyophilized whole plasma preparations. Glucose is a reducing sugar that causes protein glycation and inactivation via the Mailard reaction. This reaction involves protein amino groups reacting with glucose to form a Shiff base and Amadori products. The Mailard reaction is considered extremely deleterious for lyophilized proteins. Therefore, glucose and other reducing sugars are generally avoided in lyophilized protein formulations. However, glucose is a natural plasma constituent, which is also included in all anticoagulants used for plasma collection. (Generally referred to as ACD and CPD- or acid citrate-dextrose or citrate-phosphate-dextrose). We measure reduced glucose levels in lyophilized whole plasmas subjected to accelerated aging. Pre-lyophilization glucose concentration in plasma is approx. 334.4±10 mg/dl. After lyophilization, and consequent storage of plasma at 40° C. for 6 days, the glucose concentration is significantly reduced (approx. 290±7 mg/dl). The reduced glucose levels in lyophilized and stored plasmas, we attribute to the fact that glucose, being a reducing sugar, binds to plasma proteins in lyophilized state, and the latter results in a reduced concentration of free glucose in plasma. Protein glycation by glucose in lyophilized plasma may be a main damaging factor to plasma proteins. Accordingly, there is a challenge to develop lyophilized plasma preparations with suitable anti-coagulant protection that is not dependent on glucose/dextrose based anticoagulants.

Numerous stabilization approaches, utilizing various lyoprotectants, have been undertaken to prepare lyophilized factors VIII, IX or fibrinogen. There are, however, no reported stabilization approaches for the preparation of lyophilized whole plasma. The challenge is to stabilize not an individual protein but a complex system consisting of coagulation factors and inhibitors thereby maintaining the balance in the system.

Accordingly, it is desired by those of skill in the art to have a lyophilized whole plasma preparation that can be reconstituted in a short time frame possibly with water, that exhibit properties the same or similar to that of frozen plasma.

SUMMARY OF THE INVENTION

The present invention addresses the problems and disadvantages associated with current strategies and designs and provides new tools and methods for preserving and storing plasma.

Accordingly, in an embodiment, a plasma preparation comprises lyophilized, glycine stabilized whole plasma configured for reconstitution with water.

In an embodiment, the preparation further comprises at least one protectant selected from the group consisting of calcium chloride, trisodium citrate, HES, ammonium sulfate and/or combinations thereof.

In an embodiment, the preparation further comprises calcium chloride, trisodium citrate, HES or ammonium sulfate.

In some embodiments, the HES is amylopectin-2-hydroxyethylether.

In some embodiments, the water is selected from the group consisting of distilled, deionized, distilled-deionized, autoclaved, sterile saline, and ultra pure pathogen free water and/or combinations thereof.

In an embodiment, the plasma is autologous.
In an embodiment, the plasma is allogenic.
In some embodiments, the preparation can be reconstituted with water to approximate the original volume of the pre-lyophilized plasma.

In some embodiments, the preparation can be reconstituted with water to approximate 50% of the original volume of the pre-lyophilized plasma.

A method for preparing freeze-dried plasma according to an embodiment comprises adding glycine to sterile, pathogen free plasma under sterile conditions, freeze drying said glycine comprising sterile pathogen free plasma under conditions that suppress recrystallization of glycine, and storing the lyophilized product.

In some embodiments, a method further comprises freezing the plasma by loading the plasma at room temperature into a freezable container, placing the freezable container into a lyophilizer, freezing the plasma to −4° C. at 2° C. per minute, holding the temperature for 10 minutes, freezing the plasma to −40° C. at 1° C. per minute, and holding the temperature for 120 minutes.

In some embodiments a method further comprises drying the plasma by setting the lyophilizer chamber pressure to 0.6 mbar, increasing the temperature to 20° C. at 0.2° C. per minute, holding for 10 hour, reducing the chamber pressure to 0.0 mbar, and holding the temperature at 20° C. for 7 hour.

A system for lyophilizing plasma according to an embodiment comprises a blood-collection bag, tubing, and a freeze-dry tray, wherein the tubing fluidly connects the blood collection bag and the freeze dry tray in a substantially sterile manner.

In some embodiments, the blood-collection bag comprises an amount of a blood component. In some embodiments, the blood component is transferred from the blood-collection bag to said freeze-dry tray. In some embodiments, the blood component in the freeze-dry tray is lyophilized. In some embodiments, up to one liter of plasma is lyophilized. In some embodiments, the blood component is transferred to a second blood-collection bag reversibly connected to the freeze-dry bag. In some embodiments, the second blood-collection bag is sealed.

Other embodiments and advantages in accordance with the invention are set forth in part in the description, which follows, and in part, may be obvious from this description, or may be learned from the practice of the invention.

DESCRIPTION OF THE INVENTION

Preservation of blood plasma can be performed by many different conventional processes that maintain the basic components of the plasma, but do not preserve the integrity or functionality of proteins and other macromolecules themselves. It has been surprisingly discovered that plasma can be lyophilized and the overall integrity of the plasma and the components therein can be stabilized by lyophilizing in the presence of glycine. Plasma lyophilized according to the invention can also be reconstituted with water, a saline solution or another suitable buffer, and exhibit physiological characteristics comparable to control or untreated plasma.

According to the process of the invention, plasma to be stabilized can be autologous, allogenic or a combination thereof. In an embodiment of the invention, glycine can preserve the function of a plasma protein matrix. In a preferred embodiment, plasma protein matrix can comprise complex proteins. In another embodiment, glycine can prevent recrystallization. In this regard, glycine has been shown to be superior to other recognized "polyol" stabilizers for lyophilized plasma. Another embodiment further comprises the use of glycine as a stabilizing agent to facilitate the preparation of "protectant cocktails."

Figure 1:
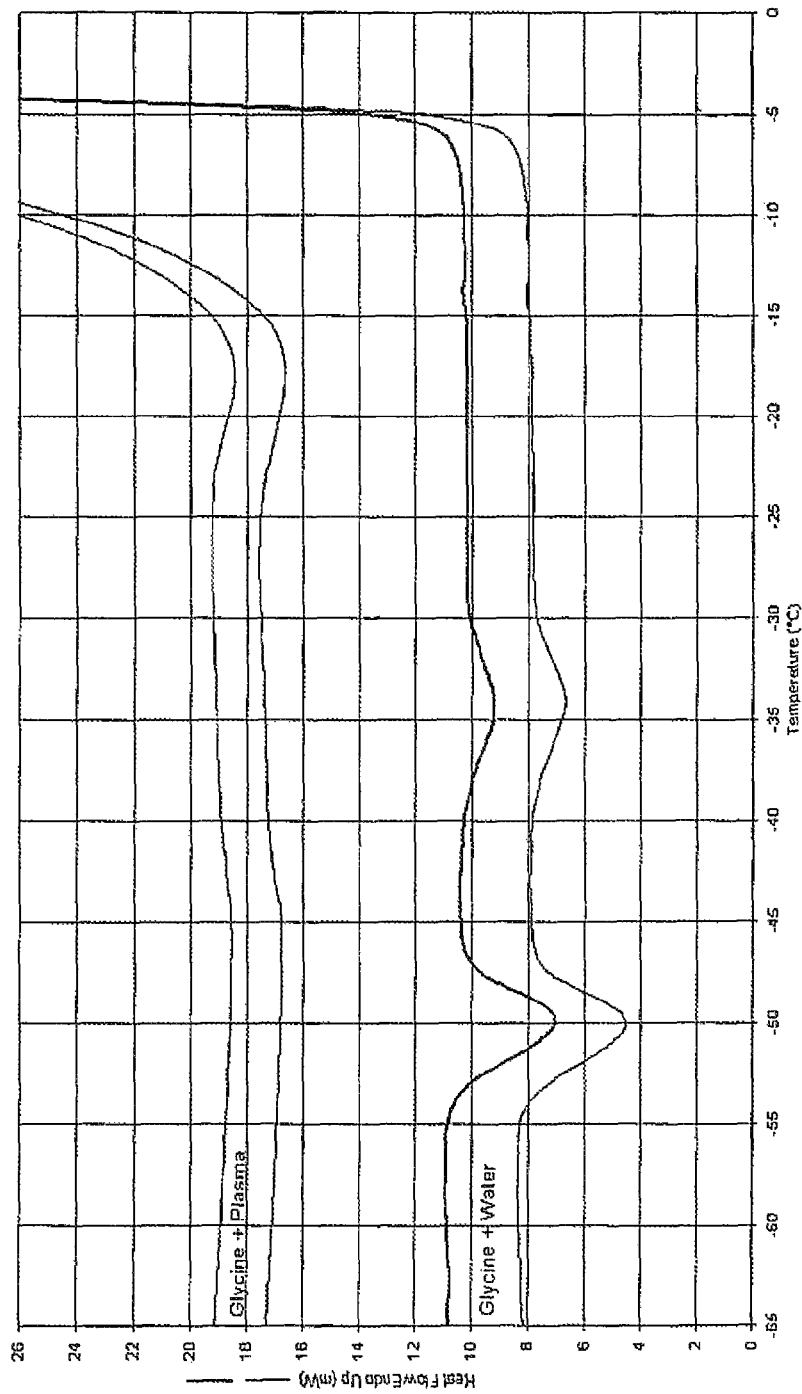
FIG. 1 is a graphic representation of the results of DSC Thermograms of glycine in a 0.5% solution in water, and in plasma.

FIG. 1 shows the difference in behavior of glycine in plasma when compared to glycine in water. Using differential scanning calorimetry, it can be seen that whole human plasma inhibits glycine crystallization during freezing. Thus, in an embodiment according to the invention, glycine can act as a protein stabilizer, in the presence of plasma, during freeze drying by remaining amorphous. The freeze drying protocol according to the invention minimizes recrystallization events thus inhibits crystallization of glycine during. This assures that glycine remain amorphous. This is a surprising because glycine is a poor candidate for use as a stabilization agent because it is well characterized as a crystallizing agent. The surprising failure of glycine to crystallize is attributable to the relatively high NaCl concentration in plasma.

Another feature of the invention is reconstitution of lyophilized plasma. In another feature of the invention, lyophilized plasma is reconstituted with water. For purposes of the invention, "water" includes, but is not limited to distilled, deionized, distilled-deionized, autoclaved, sterile saline, ultra pure pathogen free water and/or combinations thereof. In a further embodiment, lyophilized plasma can be reconstituted to 50% of its original volume. In this illustrative form, increased functionality of the reconstituted plasma can be seen. In another embodiment, glycine stabilized lyophilized plasma can be combined with at least one of tri-sodium citrate, calcium chloride, hydroxyethyl starch (HES), ammonium sulfate and combinations thereof which can serve as cryoprotectants. In another embodiment, the HES can be amylopectin-2-hydroxyethylether. In a preferred construction, citric acid can be added to maintain physiological pH. Also surprisingly, the addition of citric acid does not adversely effect the stability of the of the plasma preparation.

Further still, in an embodiment according to the invention, a system for lyophilizing plasma comprises a blood collection bag, tubing and a freeze dry tray wherein the tubing fluidly connects the blood collection bag and the freeze dry tray in a substantially sterile manner. In another embodiment, the blood bag comprises a blood component. For purposes of the invention, blood component includes but is not limited to whole blood, plasma, red bloods cells, white blood cells and platelets. In another embodiment, a blood component is transferred from the blood bag to the freeze dry tray. In still another embodiment, the blood component in the freeze dry tray is lyophilized. In yet another embodiment, up to 1 liter of plasma can be lyophilized. In yet still another embodiment, the freeze dried blood component can be transferred to a second blood bag that is reversibly connected to the freeze dry bag. Further still, the second bag may be sealed.

This invention may be further understood by reference to examples set forth below, which both describe preparation of the glycine-stabilized lyophilized plasma of the invention and its stability in terms of performance and protein activity. The following examples illustrate embodiments of the invention, but should not be viewed as limiting the scope of the invention.

EXAMPLES

Plasma Supply

Fresh donor plasma (FDP) units were obtained, frozen and stored at −80° C., and used within three months of donation. At the time of the experiments, the plasma was rapidly thawed at 37° C. in a plasma thawer and processed immediately.

Reagents

The following reagents were used: sorbitol, mannitol, glycine, ammonium sulfate, calcium chloride (dehydrate), sodium citrate (tribasic, dehydrate), citric acid, ascorbic acid, sucrose and trehalose. Water, for purposes of the instant invention, includes but is not limited to distilled, deionized, distilled-dionized, autoclaved, sterile saline, ultra pure pathogen free and combinations thereof.

Experimental Design

1. Citric acid or ascorbic acid can be added to plasma at concentrations of between 1 and 6 mM. The pH of the plasma samples can be measured before and after lyophilization to determine the concentration of citric acid or ascorbic acid needed to maintain plasma pH within the physiological range of 7.3-7.5.

2. Plasma can be supplemented with sucrose, trehalose, mannitol, sorbitol, or glycine, as a stabilizer, at a final concentration of 60 mM. In addition to each of the stabilizers, citric acid can be added at a final concentration of 2 mM, Supplemented and non-supplemented plasma can be lyophilized. The lyophilized plasma samples can be subjected to accelerated aging to determine the efficacy of the different additives that can act as a stabilizer for plasma proteins. The conditions for accelerated aging can be storage for 6 days at 40° C. The most effective stabilizer can then be used to set up samples for real time stability studies at room temperature (22° C.).

3. Ammonium sulfate can be added to plasma at concentrations of from 1.5-8 inn Plasma can then be lyophilized and subjected to accelerated aging for 6 days at 40° C.

4. Calcium chloride can be added to plasma at concentrations of from 2.5-5 mM. Plasma can then be lyophilized and subjected to accelerated aging at 40° C. for 6 days. After the accelerated aging procedure, rehydration can be performed in water. Control non-treated plasma can be lyophilized, subjected to accelerated aging at for 6 days at 40° C. and can be rehydrated either in water or in calcium chloride solutions.

5. Trisodium citrate can be added to plasma at a final concentration of from 2-10 mM. PT, APTT and TT can be measured. Plasma supplemented with 5 mM trisodium citrate can be lyophilized and subjected to accelerated aging at 40° C. for 6 days. Plasma can be rehydrated with either 2.5 mM calcium chloride or 5 mM calcium chloride to reverse the anticoagulant effect of trisodium citrate.

6. HES can be added to plasma at concentrations of from 1-3% (wt./vol). Plasma can then be lyophilized and subjected to accelerated aging for 6 days at 40° C.

7. Stabilization cocktails can be designed from at least one of the most effective stabilizer and can be added to plasma. Plasma samples supplemented with at least one of a stabilization cocktail can be lyophilized. The lyophilized samples can then be subjected to accelerated aging for 6 days at 40° C. for stabilization efficacy testing.

8. Alternatively, plasma can be supplemented with 0.5% (wt./vol) glycine and 2 mM citric acid, lyophilized and then can be stored for five months at room temperature. Non-supplemented FFP can serve as a control. Three different rehydration procedures can performed after the 5 months at room temperature:

1. 100% Rehydration: Lyophilized plasma can be reconstituted with water to 100% of its original volume.

2. 50% Rehydration: Lyophilized plasma can be reconstituted with water to 50% of its original volume. This mode of reconstitution can produce a concentrated plasma product with twice the solute concentration.

3. 50-100% Rehydration: Preparation (2) can be kept for 1 h at room temperature after which, the remaining 50% water can be added to the concentrated preparation to reach the original 100% plasma volume. This test can be performed to determine weather a transient exposure of plasma proteins to an increased salt concentration can damage the coagulation factors.

Freeze Drying and Storage

Freeze drying of a stabilized plasma was performed on a mid-scale TelStar lyophilizer. Five milliliter aliquots of plasma were transferred to siliconized glass bottles and were placed on the shelf of the lyophilizer at room temperature. The following protocol was then used to freeze dry the samples:

Freezing:

1. Load at room temperature, shelf to −4° C., 2° C./min; hold for 10 min

2. Shelf to −40° C. at 1° C./min; hold for 120 min

Primary Drying:

3. Set chamber pressure to 0.6 mbar; Ramp shelf temperature to +20° C. at 0.2° C./min. Hold for 10 h.

Secondary Drying:

4. Set Chamber pressure to 0.0 mbar; Hold at +20° C. for 7 h.

After completion of the freeze drying process, the siliconized glass bottles were sealed with rubber stoppers under vacuum inside the chamber. The lyophilized samples were subjected to accelerated aging for 6 days at 40° C. in order to determine the efficacy of the different stabilizers or cocktails.

Rehydration

The amount of water necessary for reconstitution was determined as follows:

Liquid plasma, pre-lyophilized, (5 ml plasma per bottle) and the post-lyophilized plasma samples were weighed and averaged. Weight determination was performed on 56 bottles and the mean weight difference provided an indicator of the amount of water needed for rehydration. Freeze dried plasma was rehydrated using 4.7 ml of ultra pure reagent grade water per bottle to recover 100% of the original plasma volume. Freeze dried plasma was rehydrated using 2.35 ml of water to recover 50% of the original plasma volume. All 5 mM trisodium citrate containing samples were reconstituted in 5 mM calcium chloride.

Coagulation Assays In Vitro

Figure 2:
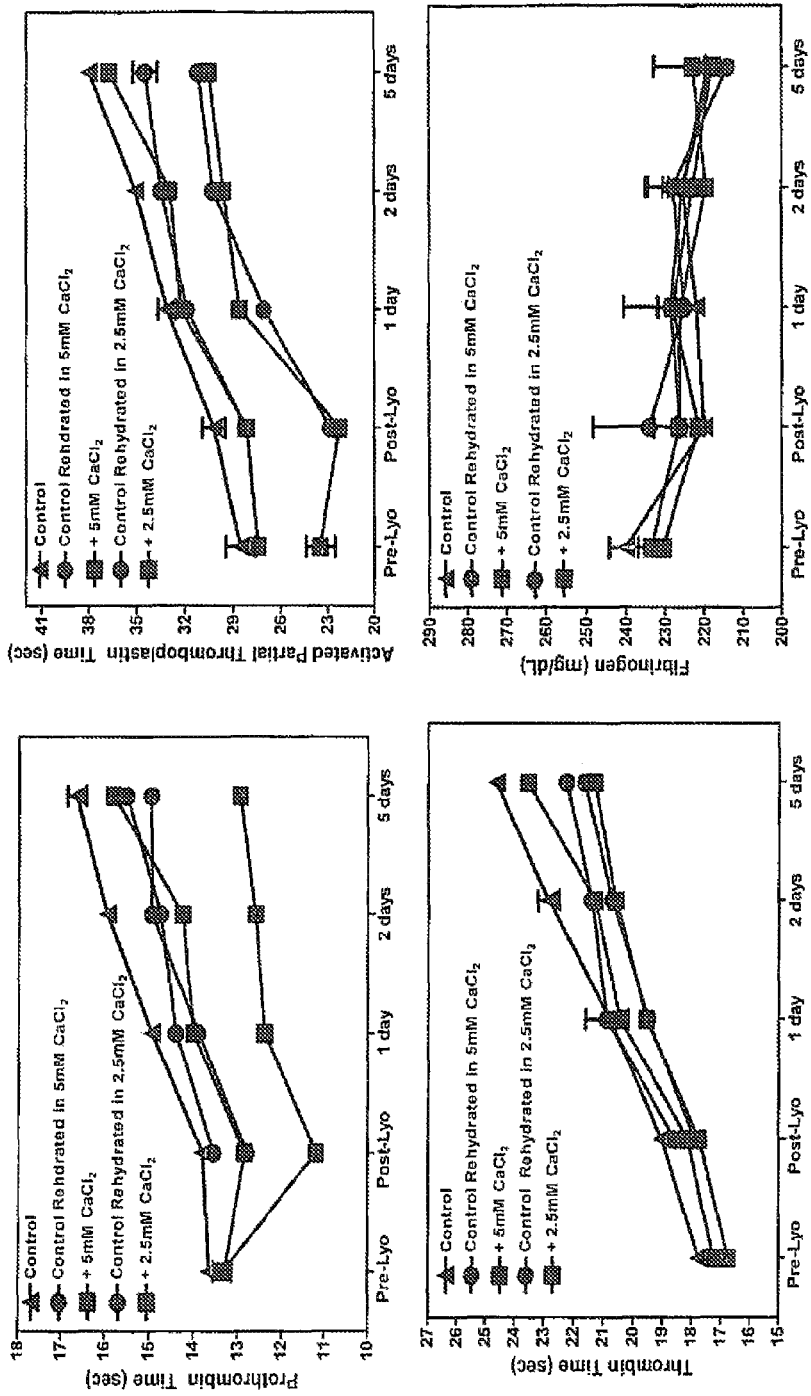
FIG. 2 is a graphic representation of the effects of the addition of calcium chloride on the stability of lyophilized plasma.
Figure 3:
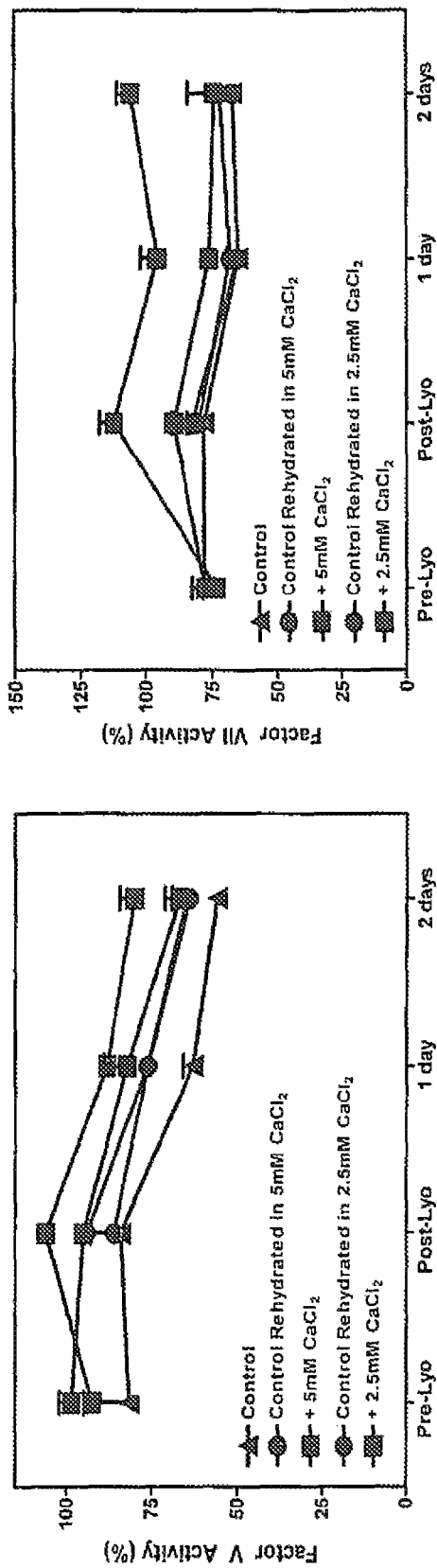
FIG. 3 is a graphic representation of the effects of the addition of calcium chloride on the stability of Factors V and VII in lyophilized plasma.
Figure 4:
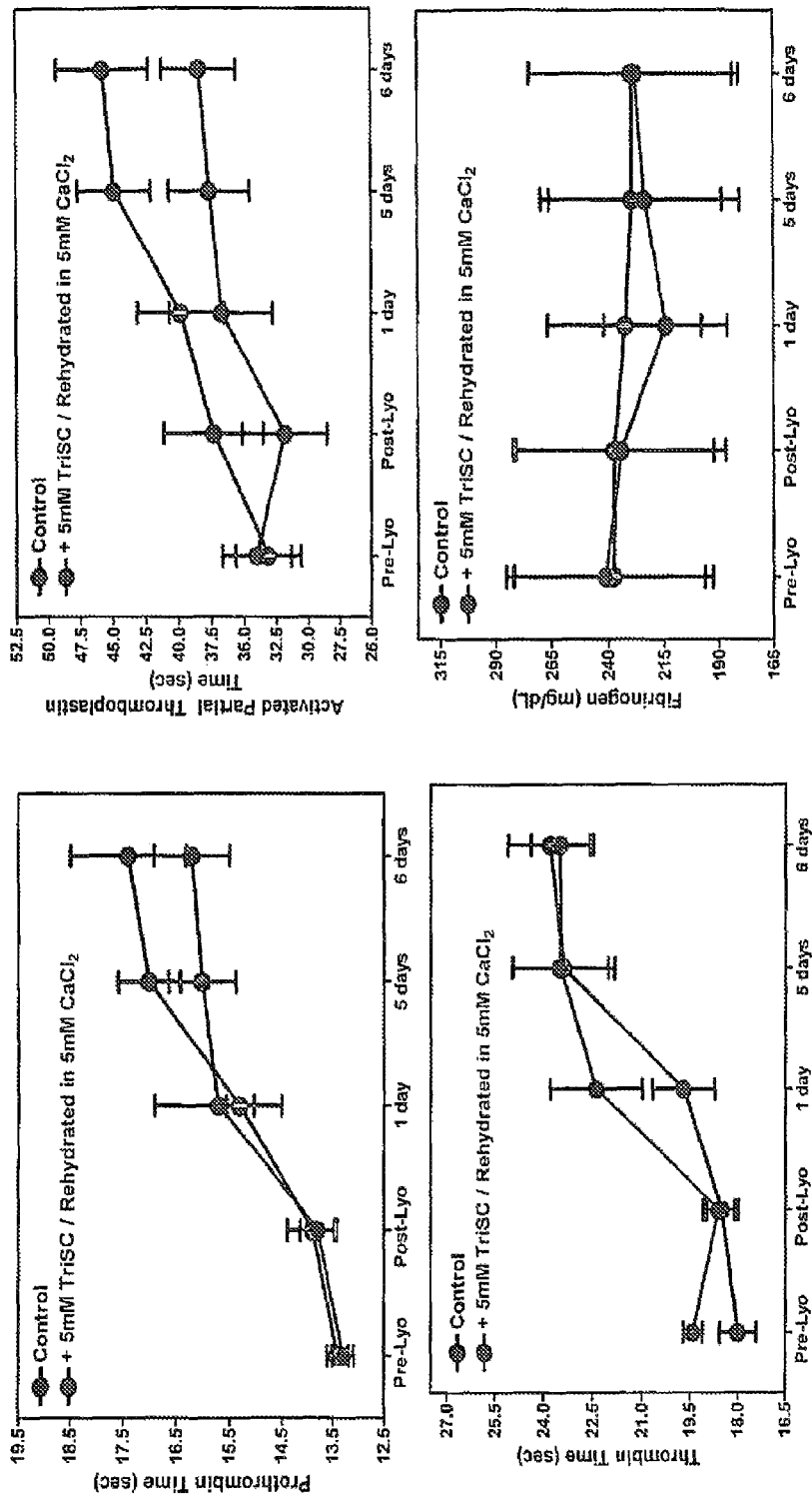
FIG. 4 is a graphic representation of the effect of the addition of tri-sodium citrate and calcium chloride on the stability of lyophilized plasma.

An automated coagulation instrument; the STA-R was used for in vitro testing of the coagulation system. Prothrombin time (PT), activated partial thromboplastin time (APTT) and thrombin time (TT), were calculated in seconds, fibrinogen was measured in mg/dL and factor V, VII, VIII, IX and X percentage activity were determined according to standard procedures. Percentage activity of Protein C, Protein S and Antithrombin III were also measured. Low and high limits were set by the corresponding controls for each test. All tests were carried out at 37° C. As can be seen from FIGS. 2 and 3, the addition of calcium chloride, improves stability and performance of the reconstituted plasma. Similar results are observed for the further addition of trisodium citrate as can be seen in FIG. 4.

Figure 5:
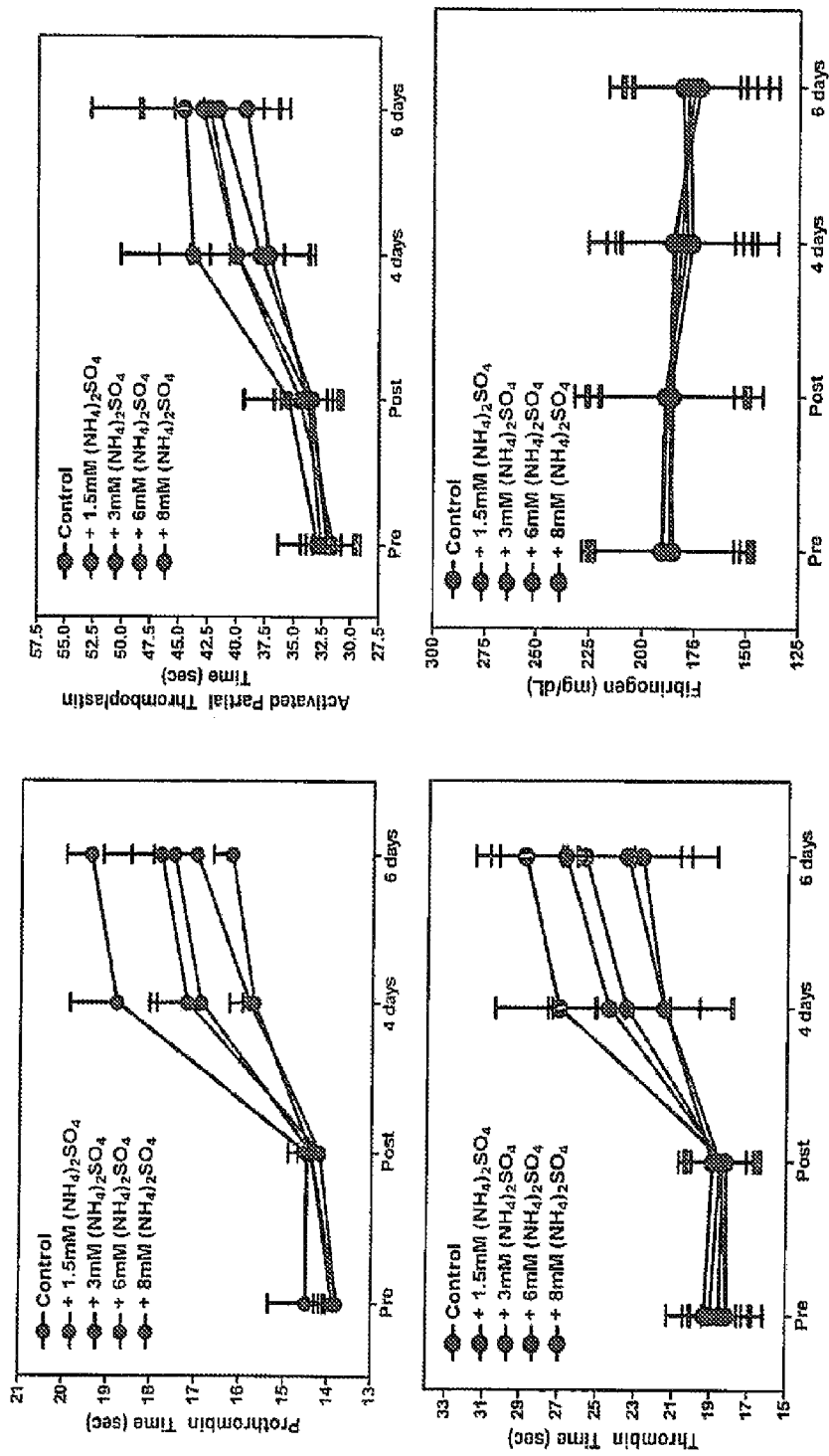
FIG. 5 is a graphic representation of the effect of the addition of ammonium sulfate on the stability of lyophilized plasma.
Figure 6:
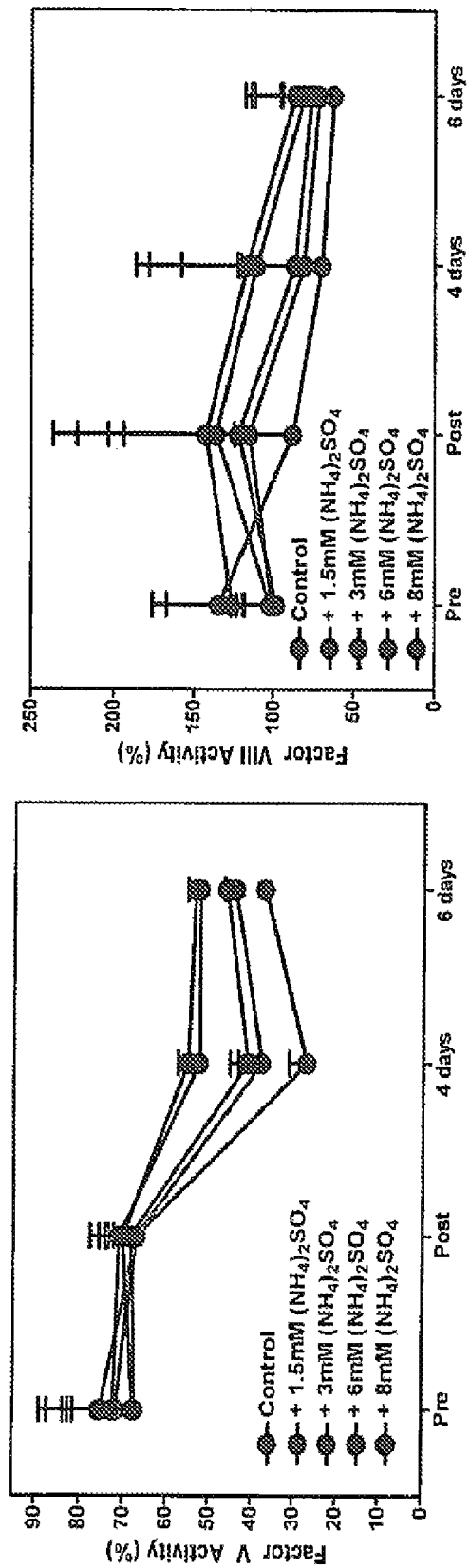
FIG. 6 is a graphic representation of the effect of the addition of ammonium sulfate on the stability of Factors V and VIII lyophilized plasma.
Figure 7:
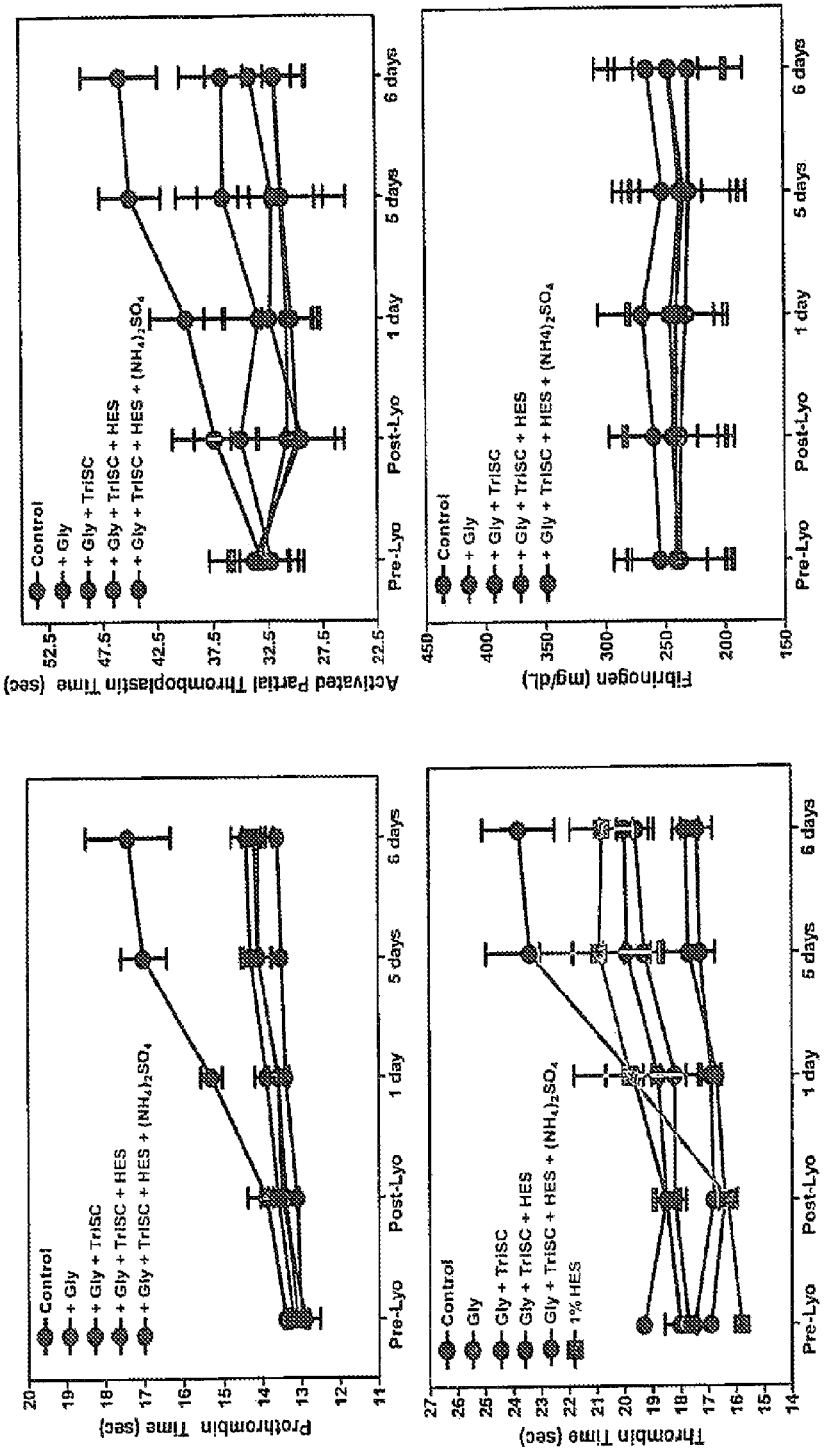
FIG. 7 is a representation of the effect of the addition of glycine-based protectant cocktails on the stability of lyophilized plasma.
Figure 8:
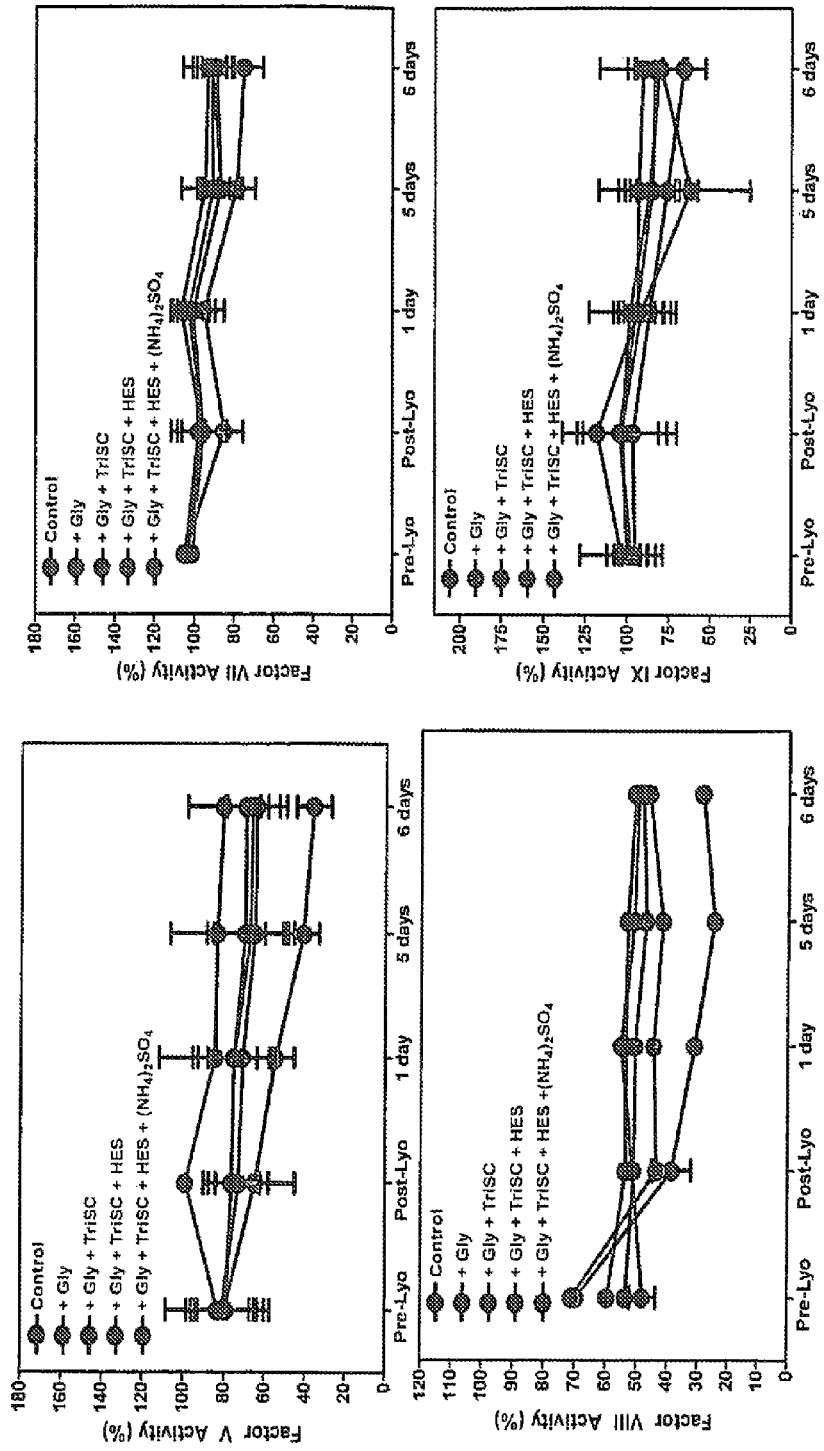
FIG. 8 is a representation of the effect of the addition of glycine-based protectant cocktails on the stability of Factors V, VII, VIII and IX in lyophilized plasma.
Figure 9:
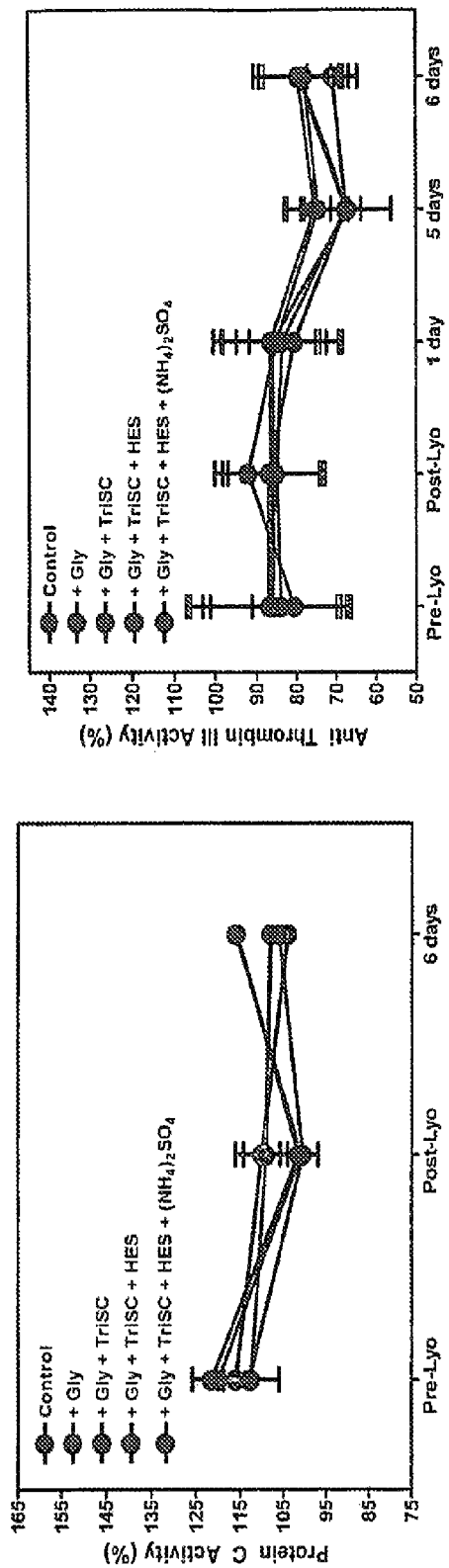
FIG. 9 is a representation of the effect of the addition of glycine-based protectant cocktails on the stability of coagulation inhibitors in lyophilized plasma.

As can be seen in FIGS. 5 and 6, the beneficial effects of the addition of ammonium sulfate is demonstrated for each of the indications measured. As shown in FIGS. 7-11, further benefits can be achieved by providing protectants for glycine stabilized lyophilized plasma in the form of a mixed cocktail of trisodium citrate, HES, ammonium sulfate and calcium chloride. Independently as well as in combination, these protectants can improve the stabilizing action of glycine and can further stabilize physiologic pH without significant increases in plasma osmolality.

There are a variety of alternatives to avoid the damaging effects of glucose functioning as an anti-coagulant. In this regard, an anti-glycating agent can be used to inhibit protein glycation in the lyophilized state. Anti-glycating agents can be used in this manner for this application including but not limited to: guanidine, aminoguanidine, carnosine, vitamin B1 and B6, Current data shows that aminoguanidine provides a substantial protection for plasma coagulation factors in lyophilized state. Lyophilized plasma shows Factor V and VIII activity of about 40 and 43%, respectively, in plasma stored for 6 days at 40° C. This activity increases to approximately 55 and 60% for Factor V and VIII, respectively, in lyophilized plasma, supplemented with 10 mM aminoguanidine under the same storage conditions.

Figure 10:
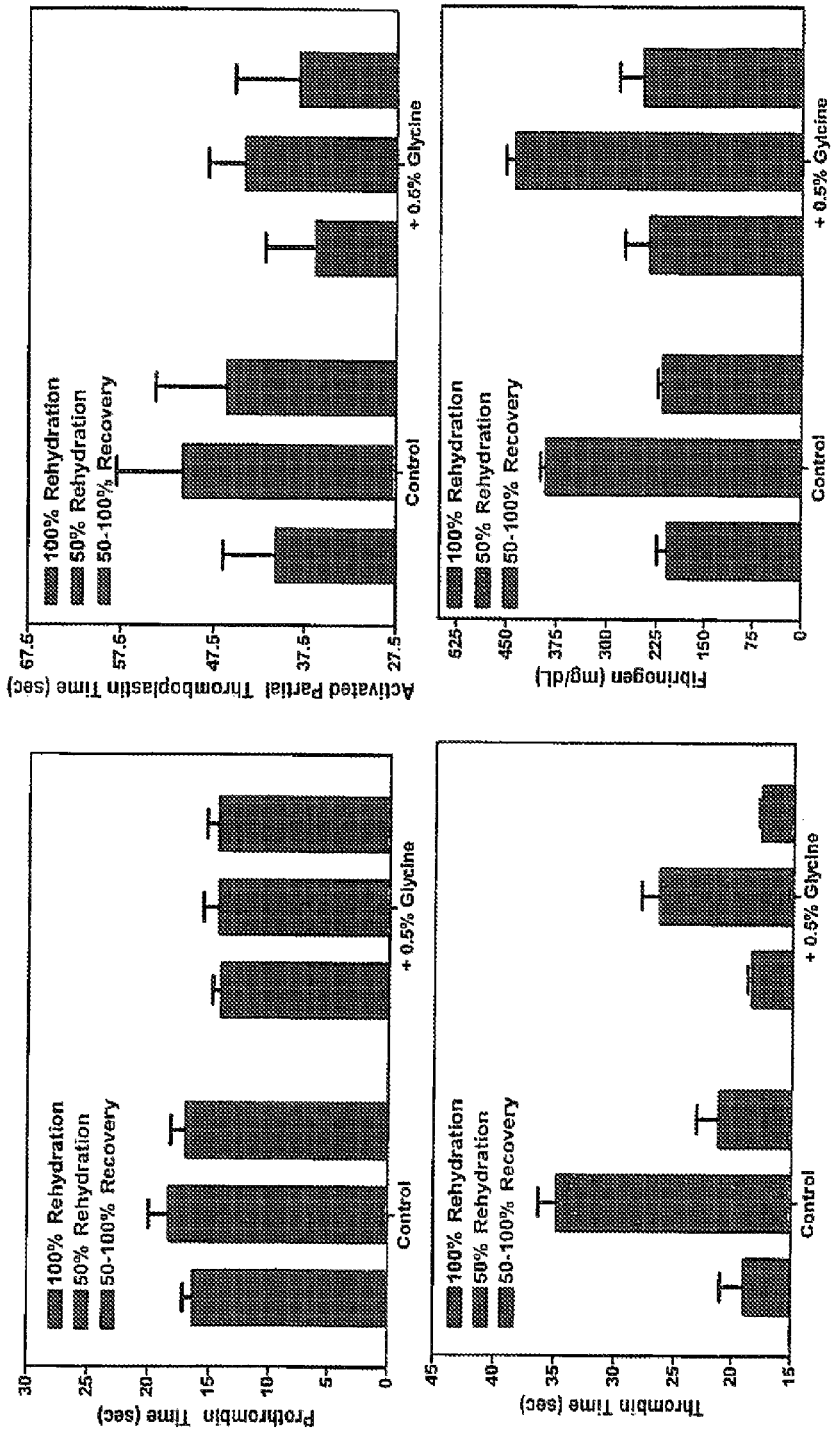
FIG. 10 is a graphic representation on the effects of the concentration of reconstituted lyophilized plasma on plasma clotting factors.
Figure 11:
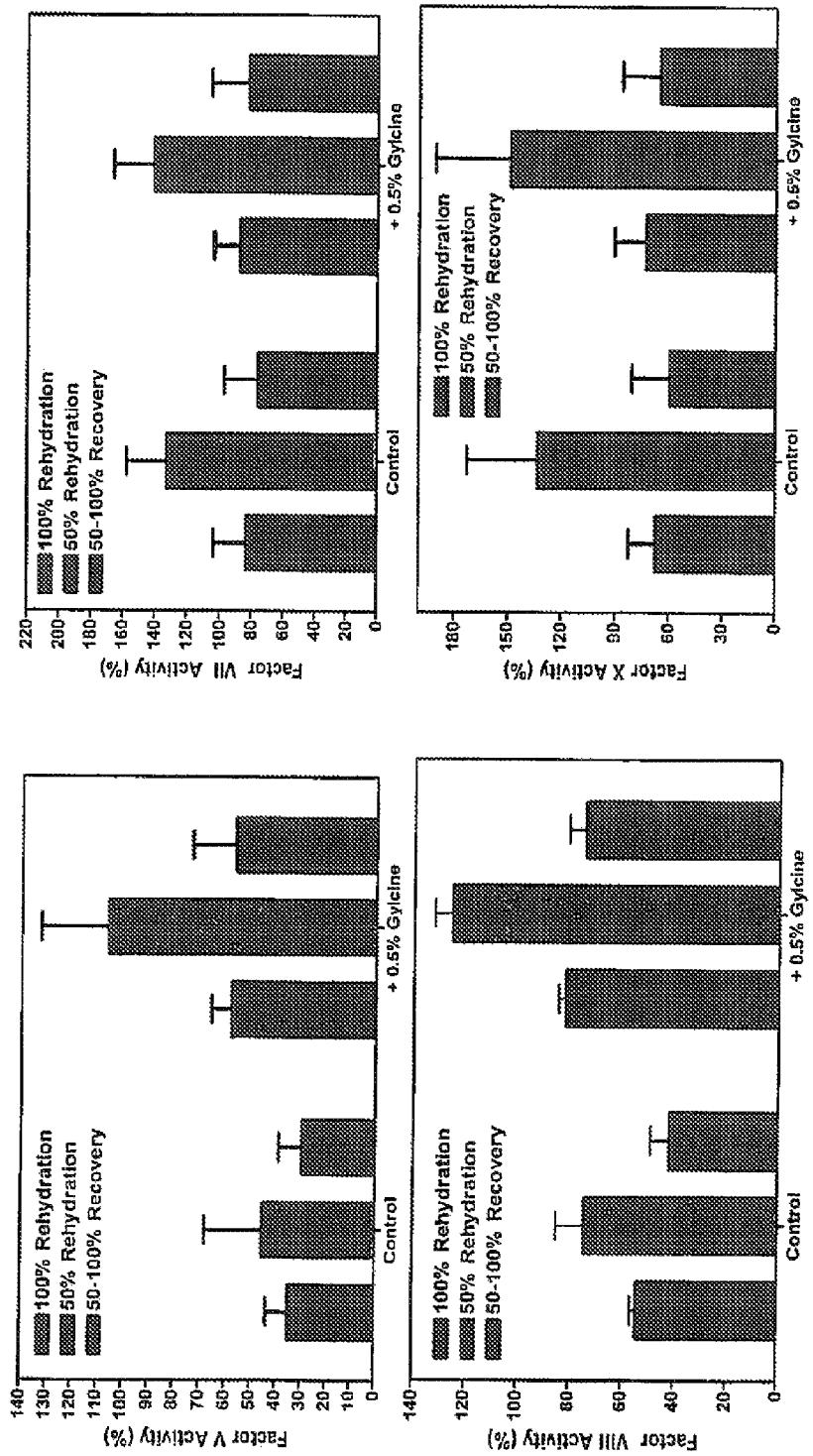
FIG. 11 is a graphic representation on the effects of the concentration of reconstituted lyophilized plasma coagulation factors V, VII, VIII and X.
Figure 12:
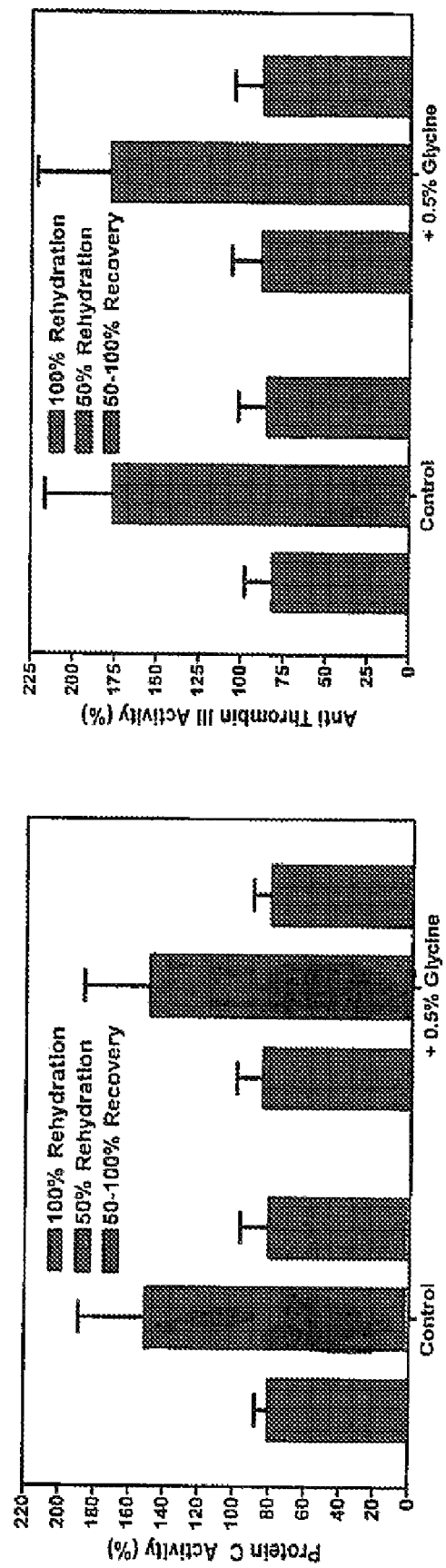
FIG. 12 is a graphic comparison of the effect of the concentration of reconstituted lyophilized plasma on coagulation inhibitors.
Figure 13:
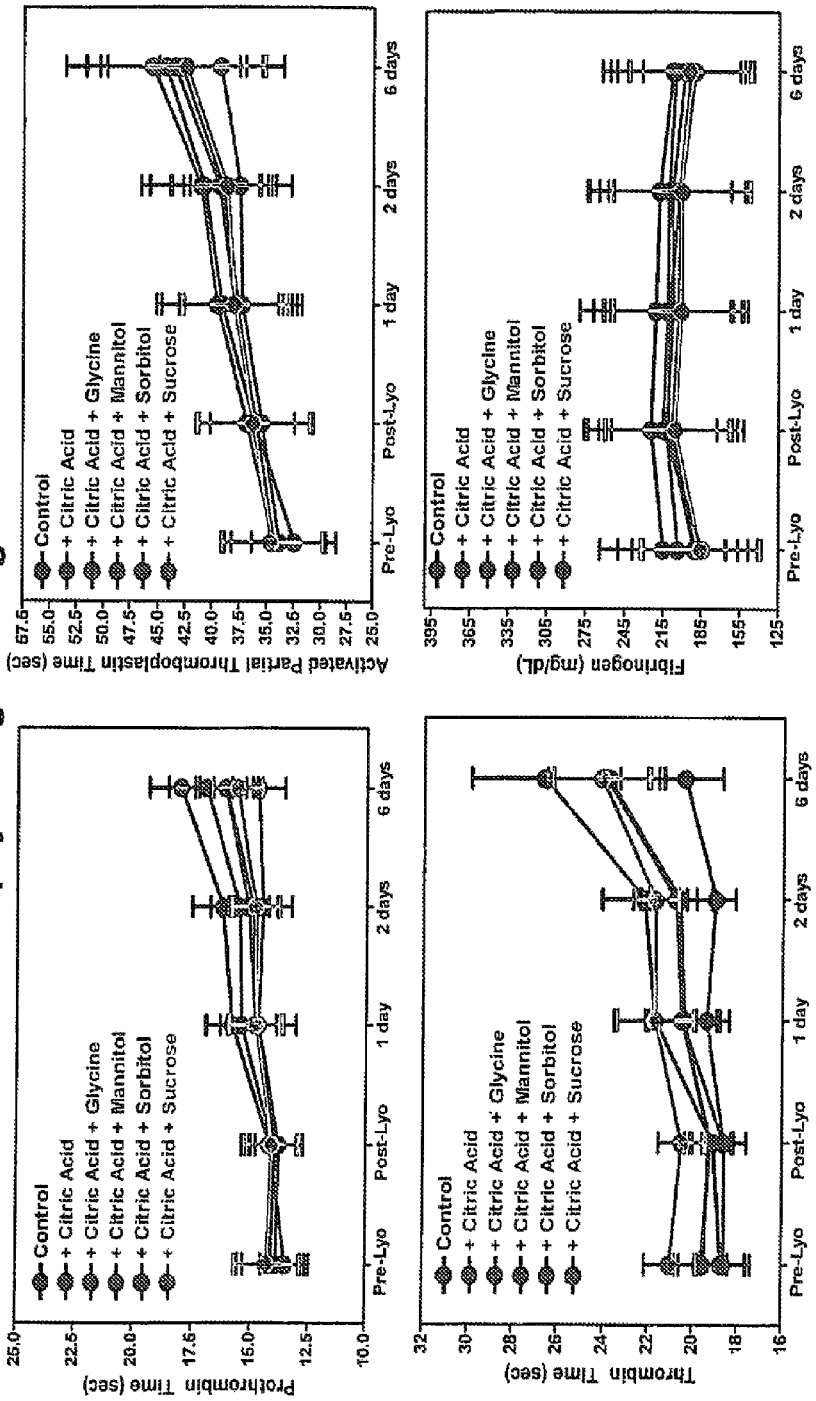
FIG. 13 compares the effect of glycine with other stabilizers on the stability of lyophilized plasma.

Glycine stabilized lyophilized plasma of the invention can be reconstituted to a 50% of total volume value. Turning now to FIGS. 10-12, preparations according to the invention wherein glycine has been added to the plasma prior to lyophilization show improved performance when reconstituted with distilled water to 50% of the original volume compared to 100% of the original volume. For instance, concentrating reconstituted plasma can be effective for increasing coagulation factor activities, such as Factor V and VIII, which remain well preserved in the glycine stabilized 50% reconstituted product. The addition of other protectants can further improve performance.

$Na^+$, $K^+$, $Cl^-$, $pCO_2$ and pH

Plasma chemical characteristics were measured using a Corning 855 clinical blood gas analyzer. The Corning 855 uses ion selective electrodes to determine $pCO_2$, pH, $Na^+$, $K^+$ and $Cl^-$ levels in plasma.

Total Protein, Phosphates and Glucose Concentrations

Total protein, phosphates and glucose concentrations in plasma were determined using an ACE clinical chemistry analyzer. Sample processing was performed according to the manufacturers standard operating procedures.

Osmolality

Osmolality was determined by freezing point depression using an Advanced Instruments Model 3900 Osmometer. Results were defined as the osmoles of solute particles per kilogram of pure solvent and expressed as mOsmol/kg.

Moisture Content

Moisture content was determined by the loss-on-drying (LOD) method using a Sartorius MA50 Moisture Analyzer. Sample preparation and testing took place in a controlled environment glove box that was continuously purged with dry nitrogen to keep relative humidity near 0%. Data was reported in percent moisture, i.e. the ratio of the weights pre and post heating.

Statistical Analysis of Data

Data were reported as mean values±S.D. Statistical significance of differences between means were calculated using a paired t-test analysis. P values were expressed at the 95% confidence level. Statistical significance was at the $P \leq 0.05$ level.

Preparation of Sterile, Freeze Dried Plasma

Glycine stabilized lyophilized plasma according to the invention, or other freeze dried, sterile preparation of whole plasma, can be advantageously prepared as described herein, infra.

An enclosed lyophilization container, the LYOGUARD Tray, can be adapted to incorporate a standard blood bank tubing line thus providing sterile transfer of glycine stabilized lyophilized plasma or other blood fluids from collection blood bags into the tray. Up to 1 liter of plasma can be lyophilized in the LYOGUARD Tray on the shelf of a freeze-dryer following a 24 h long freeze-drying cycle to assures well preserved activities of plasma coagulation proteins in the lyophilized state. The freeze-dried plasma cake is then broken into chunks by shaking the tray and transferred into a specially designed plasma bag. The plasma bag incorporates an open ring on its bottom, which can be screwed on top of the LYOGUARD Tray assuring a tight fit between the tray and the plasma bag thus allowing for a direct, sterile transfer of the freeze-dried product from the tray into the plasma bag. The plasma bag can be filled up to a pre-determined mark with the freeze-dried product then heat-sealed to cut off the ring-containing compartment. The plasma bag containing the dry plasma is finally packaged inside a moisture resistant over-pouch.

The LYOGUARD Tray is adapted to incorporate a standard blood bank tubing line thus making sterile transfer of blood fluids from collection blood bags into the tray possible. Sterile attachment of the plasma bag to the LYOGUARD tray is accomplished via the welding device. Plasma is then transferred from the collection bag into the tray.

A plasma bag is designed to incorporate an open ring on its bottom, which can be screwed on top of the LYOGUARD Tray in place of its cap thus assuring a tight fit between the tray and the plasma bag and allowing for a direct, sterile transfer of the freeze-dried product from the tray into the plasma bag. The plasma bag can have a ring. The plasma bag can be screwed on top of the LYOGUARD Tray. The plasma bag can be filled up to a pre-determined mark with the freeze-dried product then heat-sealed to cut off the ring-containing compartment. The plasma bag containing the dry plasma is finally packaged inside a moisture resistant over-pouch.

Lyophilization Cycle: Attempts to scale up the plasma lyophilization process are reported by the German Red Cross (meeting at WRAIR; product description insert). Briefly, 200 ml of plasma is lyophilized in glass or plastic bottles within 122 h applying a spin freeze-drying technology.

According to the instant invention, up to 1 L of plasma can be lyophilized, within 24 h, in an enclosed LYOGUARD Tray. Processing the product throughout the entire procedure in an enclosed sterile environment is in line with FDA requirements for blood handling. The total duration of the lyophilization cycle meets industry requirements for a short, cost-effective manufacturing process. Initial activity of the plasma proteins is well preserved in the lyophilized state (Table 1). Cycle description:

Freezing:

1. Load at room temperature, shelf to −4° C., 2° C./min; hold for 10 min.
2. Shelf to −40° C. at 1° C./min; hold for 120 min.

Primary Drying:

3. Set Chamber pressure to 0.6 mbar; Ramp shelf temperature to +20° C. at 0.2° C./min. Hold for 10 h.

Secondary Drying:

4. Set Chamber pressure to 0.0 mbar; Ramp shelf temperature to +25° C. at 0.5° C./min; Hold for 7 h.

It is understood that while the invention has been described in conjunction with the detailed description thereof, the foregoing description is intended to illustrate and not limit the scope of the invention, which is define by the scope of the appended claims. Other aspects, advantages and modifications are within the scope of the following claims.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only.

This invention has been described by reference to generic practices, and by description through specific examples. The examples are not intended to be limiting, alternatives, in terms of reagents, times and temperatures, will occur to those of skill in the art without the exercise of inventive faculty. Such alternatives remain within the scope of the invention disclosed herein, save for exclusion by express limitation in the claims set forth below.

Examples

Table 1: Three LYOGUARD trays were filled each with 800 ml SD-treated, pathogen inactivated plasma (OctaPlas) and placed on the shelves of a TELSTAR Freeze-Dryer. Lyophilization followed. The Lyophilized plasma was reconstituted directly in distilled water. A STA-R (Diagnostica Stago), automated coagulation instrument was used to perform the coagulation tests in vitro. Plasma was tested before and after lyophilization/rehydration. The basic coagulation parameters were unchanged by the lyophilization process. Data were compiled from the three trays and presented as mean values±SD.

Examples

Control FFP and FFP supplemented with a stabilizer at pre-determined concentrations were lyophilized and subjected to accelerated aging at 40° C., in order to evaluate the efficacy of the stabilizers. The following six preparations were made: 1. FFP supplemented with 0.5% (wt/vol) glycine, 2. FFP supplemented with 1% HES (wt/vol), 3. FFP supplemented with 5 mM trisodium citrate (TriSC), 4. FFP supplemented with 5 mM TriSC and 0.5% glycine, 5. FFP supplemented with 5 mM TriSC and 1% HES, 6. FFP supplemented with 5 mM TriSC and 0.5% glycine and 1% HES. Preparations 1 and 2 were reconstituted in water. All trisodium citrate containing preparations (3-6) were reconstituted in 5 mM $CaCl_2$. $CaCl_2$ was added to offset the anticoagulant, $Ca^{++}$ chelating effect of trisodium citrate.

TABLES 2-3 show that all stabilizers preserve the basic coagulation characteristics (PT, aPTT, TT, FIB). The most potent individual stabilizer is glycine. The most potent combination of stabilizers is preparation 6: +5 mM TriSC+ 0.5% glycine+1% HES.

TABLE 2: Effect of lyophilization and consequent heat treatment at 40° C. on Prothrombin Time (PT). Plasma products tested: Control FFP, FFP supplemented with 0.5% (wt/vol) glycine, FFP supplemented with 1% HES (wt/vol), HP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLE 3: Effect of lyophilization and consequent heat treatment at 40° C. on Activated Partial Thromboplastin Time (aPTT). Plasma products tested: Control FPP, FFP supplemented with 0.5% (wt./vol) glycine, FFP supplemented with 1% HES (wt./vol), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLES 4-8 show that all stabilizers preserve the coagulation factors tested: Factor V, VII, VIII, IX, and X. The most potent individual stabilizer is glycine. The most potent combination of stabilizers is preparation 6: +5 mM TriSC+ 0.5% glycine+1% HES.

TABLE 4: Effect of lyophilization and consequent heat treatment at 40° C. on Factor V (%) Activity. Plasma products tested: Control FFP, FFP supplemented with 0.5% (wt/vol) glycine, FFP supplemented with 1% HES (wt./vol), (FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLE 5: Effect of lyophilization and consequent heat treatment at 40° C. on Factor VII (%) Activity. Plasma products tested: Control FFP, FFP supplemented at 0.5% (wt/vol) glycine, FFP supplemented with 1% HES (wt/vol), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM and 0.5% glycine and 1% HES.

TABLE 6: Effect of lyophilization and consequent heat treatment at 40° C. on Factor VIII (%) Activity. Plasma products tested: Control FFP, FFP supplemented with 0.5% (wt./vol) glycine, FFP supplemented with 1% HES (wt./vol), FFP supplemented with 0.5 mM trisodium citrate (TriSC), FFP supplemented with 5 mM TriSC and 0.5% glycine, FFP supplemented with 5 mM. TriSC and 1% HES, FFP supplemented with 5 mM TriSC and 0.5% glycine and 1% HES.

TABLE 7: Effect of lyophilization and consequent heat treatment at 40° C. on Factor IX (%) Activity. Plasma products tested: Control FFP, FFP supplemented with 0.5% (wt./vol) glycine, PEP supplemented with 1% HES (wt./vol), FFP supplemented with 5 mM TriSC 5 mM trisodium citrate (TriSC), FFP supplemented with 5 mM TriSC and 0.5% glycine, FFP supplemented with 5 mM MSC and 1% HES, FFP supplemented with 5 mM TriSC and 0.5% glycine and 1% HES.

TABLE 8: Effect of lyophilization and consequent heat treatment at 40° C. on Factor X (%) Activity. Plasma products tested: Control FFP, FFP supplemented with 0.5% (wt./vol) glycine, FFP supplemented with 1% HES (wt./vol), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLES 9-10 show that all stabilizers preserve the coagulation inhibitors tested: Protein C and Antithrombin III. The most potent individual stabilizer is glycine. The most potent combination of stabilizers is preparation 6: +5 mM TriSC+0.5% glycine+1% HES.

TABLE 9: Effect of lyophilization and consequent heat treatment at 40° C. on Protein C (%) Activity. Plasma products tested: Control FFP, FFP supplemented with 0.5% (wt/vol) glycine, FFP supplemented with 1% HES (wt/vol), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLE 10: Effect of lyophilization and consequent heat treatment at 40° C. on Antithrombin III (%) Activity. Plasma products tested: Control FFP, FFP supplemented with 0.5% (wt/vol) glycine, FFP supplemented with 1% HES (wt./vol), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLE 11 shows that pH is substantially elevated in lyophilized plasma. Addition of glycine stabilizes pH between 7.8-7.9. Lyophilized plasma preparations without glycine have a pH≧7.9 or outside the detection limit of the clinical instrument used in this study.

TABLE 11: Effect of lyophilization and consequent heat treatment at 40° C. on plasma pH. Plasma products tested: Control FFP, FFP supplemented with 0.5% (wt./vol) glycine, FFP supplemented with 1% HES (wt./vol.), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

TABLE 12 shows that addition of the selected stabilizers at the pre-determined concentrations maintains plasma osmolality within the acceptable physiological range.

TABLE 12: Effect of lyophilization and consequent heat treatment at 40° C. on plasma osmolality. Plasma products tested: Control FFP, FFP supplemented with 0.5% (wt/vol) glycine, FFP supplemented with 1% FIES (wt./vol), FFP supplemented with 5 mM trisodium citrate (TriSC), FFP supplemented with 5 mM TriSC and 0.5% glycine, FFP supplemented with 5 mM TriSC and 1% HES, FFP supplemented with 5 mM TriSC and 0.5% glycine and 1% HES.

Examples

FFP was supplemented with 0.5% (wt/vol) glycine and 2 mM citric acid, lyophilized and stored for five months at room temperature (22° C.). Non-supplemented FFP served as a control. Citric acid was added to maintain physiological pH of the lyophilized plasma. Three modes of rehydration were performed on the lyophilized product:
1. 100% Rehydration: Lyophilized plasma was reconstituted with water to 100% of its original volume.
2. 50% Rehydration: Lyophilized plasma was reconstituted with water to 50% of its original volume. This mode of reconstitution produces a concentrated plasma product. Protein concentration, salt concentration and osmolality are expected to be two times higher in this preparation (2) compared to preparation (1).
3. 100% Recovery: Preparation (2) was kept for 1 h at room temperature then the remaining 50% water was added back to the concentrated preparation to recover the original 100% plasma volume, This test was performed to determine weather a temporally exposure of plasma proteins to an increased salt concentration would damage the coagulation factors.

TABLES 13-15 show that the basic coagulation characteristics (PT, aPTT, TT) are best preserved in the glycine/citric acid supplemented plasma. Transient exposure of plasma proteins to an increased salt content in the concentrated plasma format causes a prolongation in the PT, aPTT and TT. The effect is irreversible for the control plasma and almost fully reversible for the glycine/citric acid plasma.

TABLE 16 shows that the Fibrinogen concentration is approx, two times higher in the concentrated plasma product.

TABLES 17-21 show that Coagulation factors V, VII, VIII, IX and X are best preserved in the glycine/citric acid supplemented plasma. Concentrating plasma proteins in the concentrated plasma format increases the coagulation factor activities. Factor V and VIII activities remain well preserved in the glycine/citric acid plasma after a transient exposure to an increased salt concentration and a consequent recovery of the original plasma volume and salt content. In contrast, Factor V and VIII activities are decreased in the control plasma after a transient exposure to an increased salt concentration and a consequent recovery of the original plasma volume and salt content.

TABLES 22-24 show that the activities of the coagulation inhibitors are similar in the control and the glycine/citric acid plasma.

TABLE 25 shows that addition of 2 mM citric acid maintains plasma pH within physiological range.

TABLE 26 shows that plasma osmolality is approx. two times higher in the concentrated plasma.

Examples

FFP was supplemented with different concentrations of Ammonium Sulfate, lyophilized and stored for six days at 40° C. The ammonium sulfate concentration in plasma varied between 1.5 and 8 mM. Non-supplemented FFP served as a control.

TABLES 27-29 show that the basic plasma coagulation characteristics (PT, aPTT and TT) are well preserved in the presence of ammonium sulfate. The stabilization effect is concentration dependent. A maximal preservation effect is reached at 6 mM final concentration and a further increase in the ammonium sulfate concentration does not result in a substantial further increase in its preservation capacity.

TABLE 30 shows that presence of ammonium sulfate in plasma has no impact on the fibrinogen concentration.

TABLES 31-32 show that percent activities of factors V and VIII are well preserved, in the presence of ammonium sulfate. The stabilization effect is concentration dependent. A maximal preservation effect is reached at 6 mM final concentration and a further increase in the ammonium sulfate concentration does not result in a substantial further increase in its preservation capacity.

Examples

Set 1: Sucrose, trehalose or glycine were added to fresh frozen plasma (FFP) at 0.5% (wt./vol) concentrations, citric acid was added to all plasma preparations at a final concentration of 2 mM. Plasmas supplemented with the different additives and non-supplemented control plasma were lyophilized, and then subjected to accelerated aging storage at 40° C. for 10 days.

Set 2: Sucrose, mannitol, sorbitol or glycine were added to fresh frozen plasma (FFP) at 60 mM final concentrations. Citric acid was added to all plasma preparations at a final concentration of 2 mM. Plasmas supplemented with the different additives and non-supplemented control plasma were lyophilized, and then subjected to accelerated aging storage at 40° C. for 6 days.

Sucrose, trehalose, mannitol, sorbitol and glycine were compared for their stabilizing effect on plasma proteins in lyophilized form. glycine was found to be the most potent stabilizer. Addition of 2 mM citric acid to plasma prior to lyophilization was shown to stabilize plasma pH within the physiological range.

TABLE 1

| Parameter | Pre-Lyophilization | Post-Lyophilization | p Value |
|---|---|---|---|
| Prothrombin Tim (sec) | 14.0 ± 0.100 | 14.433 ± 0.208 | 0.133 |
| Activated Partial Thromboplastin Time (sec) | 36.733 ± 1.210 | 36.133 ± 1.012 | 0.663 |
| Thrombin Time (sec) | 18.833 ± 0.058 | 18.700 ± 0.100 | 0.270 |
| Fibrinogen (mg/dL) | 279.333 ± 1.528 | 296.333 ± 24.542 | 0.349 |

TABLE 2

| | | | | | |
|---|---|---|---|---|---|
| Control | 13.5 ± 0.115 | 14.1 ± 0.153 | 15.3 ± 0.252 | 17.5 ± 0.141 | 18.3 ± 0.707 |
| +0.5% Glycine | 13.3 ± 0.265 | 13.8 ± 0.361 | 14.0 ± 0.200 | 14.6 ± 0.000 | 14.8 ± 0.212 |
| +1% HES | 13.3 ± 0.231 | 14.1 ± 0.208 | 15.2 ± 0.473 | 17.5 ± 0.707 | 17.9 ± 0.707 |
| +5 mM TriSodium Citrate | 13.3 ± 0.252 | 13.9 ± 0.173 | 14.9 ± 0.458 | 16.5 ± 0.354 | 16.8 ± 0.424 |

TABLE 2-continued

| | | | | | |
|---|---|---|---|---|---|
| +5 mM TriSC + 0.5% Glycine | 13.2 ± 0.208 | 13.5 ± 0.252 | 13.6 ± 0.289 | 14.4 ± 0.000 | 14.5 ± 0.000 |
| +5 mM TriSC + 1% HES | 13.3 ± 0.231 | 13.9 ± 0.400 | 14.4 ± 0.379 | 16.2 ± 0.283 | 16.5 ± 0.636 |
| +5 mM TriSC + 0.5% Glycine + 1% HES | 13.1 ± 0.173 | 13.6 ± 0.208 | 13.7 ± 0.058 | 14.4 ± 0.141 | 14.4 ± 0.141 |

TABLE 3

| Plasma Product | Pre-Lyo aPTT (sec) | Post-Lyo aPTT (sec) | 1 day at 40° C. aPTT (sec) | 5 days at 40° C. aPTT (sec) | 6 days at 40° C. aPTT (sec) |
|---|---|---|---|---|---|
| Control | 33.7 ± 2.663 | 38.2 ± 4.188 | 40.0 ± 3.955 | 43.0 ± 1.768 | 44.6 ± 1.980 |
| +0.5% Glycine | 32.7 ± 3.360 | 35.7 ± 4.734 | 35.1 ± 4.028 | 33.7 ± 0.000 | 34.2 ± 0.919 |
| +1% HES | 33.6 ± 2.166 | 38.3 ± 3.554 | 40.0 ± 3.062 | 43.3 ± 3.253 | 43.6 ± 1.838 |
| +5 mM TriSodium Citrate | 34.7 ± 2.784 | 32.5 ± 3.647 | 35.0 ± 2.272 | 36.7 ± 1.697 | 37.6 ± 1.414 |
| +5 mM TriSC + 0.5% Glycine | 34.1 ± 3.073 | 30.4 ± 4.029 | 30.7 ± 3.119 | 30.4 ± 1.273 | 30.3 ± 0.354 |
| +5 mM TriSC + 1% HES | 34.8 ± 2.255 | 32.6 ± 3.482 | 34.6 ± 2.503 | 36.8 ± 2.404 | 37.3 ± 2.263 |
| +5 mM TriSC + 0.5% Glycine + 1% HES | 33.9 ± 2.802 | 31.5 ± 6.058 | 31.1 ± 3.213 | 31.1 ± 2.192 | 30.0 ± 0.636 |

TABLE 4

| Plasma Product | Pre-Lyo Factor V (%) | Post-Lyo Factor V (%) | 1 day at 40° C. Factor V (%) | 5 days at 40° C. Factor V (%) | 6 days at 40° C. Factor V (%) |
|---|---|---|---|---|---|
| Control | 72.3 ± 7.767 | 55.3 ± 5.508 | 50.7 ± 5.033 | 37.0 ± 4.243 | 31.5 ± 0.707 |
| +0.5% Glycine | 74.7 ± 6.028 | 66.0 ± 5.292 | 63.0 6.557 | 52.0 ± 0.000 | 57.5 ± 3.536 |
| +1% HES | 75.0 ± 6.083 | 61.0 ± 5.568 | 52.7 ± 6.807 | 35.0 ± 1.414 | 35.5 ± 0.707 |
| +5 mM TriSodium Citrate | 70.7 ± 3.512 | 64.3 ± 5.508 | 54.3 ± 7.234 | 42.5 ± 3.536 | 41.0 ± 2.828 |
| +5 mM TriSC + 0.5% Glycine | 72.3 ± 4.163 | 69.7 ± 3.215 | 65.3 ± 4.726 | 57.0 ± 8.485 | 59.0 ± 7.071 |
| +5 mM TriSC + 1% HES | 70.3 ± 7.572 | 67.7 ± 2.309 | 58.0 ± 5.568 | 45.0 ± 2.828 | 44.0 ± 1.414 |
| +5 mM TriSC + 0.5% Glycine + 1% HES | 70.0 ± 6.083 | 69.3 ± 2.082 | 66.7 ± 4.726 | 60.0 ± 8.485 | 64.0 ± 4.243 |

TABLE 5

| Plasma Product | Pre-Lyo Factor VII (%) | Post-Lyo Factor VII (%) | 1 day at 40° C. Factor VII (%) | 5 days at 40° C. Factor VII (%) | 6 days at 40° C. Factor VII (%) |
|---|---|---|---|---|---|
| Control | 106.0 ± 1.000 | 82.0 ± 34.699 | 96.3 ± 11.930 | 74.5 ± 7.778 | 69.5 ± 0.707 |
| +0.5% Glycine | 101.7 ± 4.041 | 96.7 ± 13.013 | 102.3 ± 13.429 | 76.0 ± 0.000 | 83.5 ± 2.121 |
| +1% HES | 99.0 ± 10.817 | 94.3 ± 14.503 | 98.0 ± 15.395 | 71.0 ± 2.828 | 73.5 ± 0.707 |
| +5 mM TriSodium Citrate | 100.3 ± 7.371 | 94.3 ± 17.502 | 93.3 ± 13.204 | 74.5 ± 4.950 | 74.0 ± 1.414 |
| +5 mM TriSC + 0.5% Glycine | 103.7 ± 3.055 | 97.0 ± 17.088 | 100.0 ± 9.849 | 83.5 ± 7.778 | 84.0 ± 1.414 |
| +5 mM TriSC + 1% HES | 101.0 ± 2.000 | 98.7 ± 16.073 | 97.3 ± 5.686 | 76.5 ± 0.707 | 75.0 ± 2.828 |

TABLE 5-continued

| Plasma Product | Pre-Lyo Factor VII (%) | Post-Lyo Factor VII (%) | 1 day at 40° C. Factor VII (%) | 5 days at 40° C. Factor VII (%) | 6 days at 40° C. Factor VII (%) |
|---|---|---|---|---|---|
| +5 mM TriSC + 0.5% Glycine + 1% HES | 104.7 ± 4.163 | 90.0 ± 9.899 | 101.0 ± 9.644 | 87.0 ± 4.243 | 86.5 ± 2.121 |

TABLE 6

| Plasma Product | Pre-Lyo Factor VIII (%) | Post-Lyo Factor VIII (%) | 1 day at 40° C. Factor VIII (%) | 5 days at 40° C. Factor VIII (%) | 6 days at 40° C. Factor VIII (%) |
|---|---|---|---|---|---|
| Control | 95.0 ± 35.35 | 66.0 ± 32.450 | 37.7 ± 7.638 | 59.5 ± 34.648 | 53.0 ± 24.042 |
| +0.5% Glycine | 98.5 ± 38.89 | 72.3 ± 32.960 | 67.3 ± 22.502 | 59.0 ± 0.000 | 85.0 ± 33.941 |
| +1% HES | 93.5 ± 37.47 | 60.7 ± 29.956 | 47.7 ± 12.014 | 47.0 ± 16.971 | 50.0 ± 21.213 |
| +5 mM TriSodium Citrate | 94.0 ± 31.432 | 71.3 ± 29.143 | 54.7 ± 17.010 | 56.5 ± 24.749 | 63.0 ± 29.698 |
| +5 mM TriSC + 0.5% Glycine | 101.3 ± 36.679 | 75.0 ± 21.517 | 75.0 ± 20.518 | 76.0 ± 36.770 | 100.5 ± 48.790 |
| +5 mM TriSC + 1% HES | 94.3 ± 36.638 | 65.0 ± 19.975 | 56.0 ± 13.115 | 55.5 ± 27.577 | 67.5 ± 26.163 |
| +5 mM TriSC + 0.5% Glycine + 1% HES | 89.0 ± 30.348 | 72.0 ± 24.556 | 73.0 ± 20.664 | 68.0 ± 19.799 | 109.5 ± 48.790 |

TABLE 7

| Plasma Product | Pre-Lyo Factor IX (%) | Post-Lyo Factor IX (%) | 1 day at 40° C. Factor IX (%) | 5 days at 40° C. Factor IX (%) | 6 days at 40° C. Factor IX (%) |
|---|---|---|---|---|---|
| Control | 93.3 ± 7.767 | 89.0 ± 16.823 | 81.7 ± 15.044 | 68.0 ± 5.657 | 57.5 ± 0.707 |
| +0.5% Glycine | 96.0 ± 3.000 | 93.3 ± 10.970 | 86.0 ± 9.165 | 86.0 ± 0.000 | 69.5 ± 2.121 |
| +1% HES | 95.0 ± 8.718 | 96.0 ± 11.269 | 81.7 ± 10.970 | 68.5 ± 3.536 | 61.0 ± 1.414 |
| +5 mM TriSodium Citrate | 97.0 ± 6.245 | 87.7 ± 5.033 | 79.7 ± 10.970 | 67.0 ± 5.657 | 61.5 ± 0.707 |
| +5 mM TriSC + 0.5% Glycine | 96.3 ± 4.726 | 90.3 ± 10.214 | 87.0 ± 12.166 | 77.0 ± 5.657 | 72.0 ± 1.414 |
| +5 mM TriSC + 1% HES | 94.0 ± 6.557 | 90.0 ± 11.533 | 83.67 ± 13.013 | 66.0 ± 9.899 | 63.5 ± 2.121 |
| +5 mM TriSC + 0.5% Glycine + 1% HES | 90.7 ± 6.506 | 88.0 ± 10.440 | 90.3 ± 9.018 | 73.0 ± 5.657 | 76.5 ± 4.950 |

TABLE 8

| Plasma Product | Pre-Lyo Factor X (%) | Post-Lyo Factor X (%) | 1 day at 40° C. Factor X (%) | 5 days at 40° C. Factor X (%) | 6 days at 40° C. Factor X (%) |
|---|---|---|---|---|---|
| Control | 86.3 ± 12.503 | 80.0 ± 16.703 | 77.7 ± 10.693 | 67.0 ± 14.142 | 62.5 ± 17.678 |
| +0.5% Glycine | 85.3 ± 14.012 | 83.0 ± 16.093 | 82.0 ± 11.533 | 84.0 ± 0.000 | 73.5 ± 17.678 |
| +1% HES | 84.3 ± 13.868 | 82.7 ± 16.258 | 77.3 ± 8.963 | 65.5 ± 14.849 | 64.5 ± 16.263 |
| +5 mM TriSodium Citrate | 84.7 ± 15.567 | 82.0 ± 13.528 | 77.3 ± 10.970 | 65.0 ± 15.556 | 65.5 ± 19.092 |
| +5 mM TriSC + 0.5% Glycine | 84.3 ± 15.275 | 83.0 ± 16.000 | 82.7 ± 13.650 | 71.5 ± 14.849 | 74.5 ± 17.678 |
| +5 mM TriSC + 1% HES | 84.0 ± 13.115 | 82.3 ± 15.567 | 78.3 ± 10.599 | 65.0 ± 15.556 | 65.0 ± 16.971 |
| +5 mM TriSC + 0.5% Glycine + 1% HES | 82.0 ± 13.115 | 83.7 ± 15.275 | 82.3 ± 12.014 | 71.5 ± 20.506 | 75.0 ± 16.971 |

TABLE 9

| Plasma Product | Pre-Lyo Protein C (%) | Post-Lyo Protein C (%) | 1 day at 40° C. Protein C (%) | 5 days at 40° C. Protein C (%) | 6 days at 40° C. Protein C (%) |
|---|---|---|---|---|---|
| Control | 116.0 ± 9.899 | 110.0 ± 4.243 | 101.5 ± 3.536 | 89.0 ± 0.000 | 104.0 ± 0.000 |
| +0.5% Glycine | 112.5 ± 6.364 | 109.0 ± 7.071 | 103.5 ± 2.121 | 104.5 ± 2.000 | 108.0 ± 0.000 |
| +1% HES | 121.0 ± 0.000 | 107.5 ± 3.536 | 101.5 ± 4.950 | 86.0 ± 0.000 | 106.0 ± 0.000 |
| +5 mM TriSodium Citrate | 119.0 ± 0.000 | 100.5 ± 0.707 | 97.0 ± 5.657 | 85.0 ± 0.000 | 101.0 ± 0.000 |
| +5 mM TriSC + 0.5% Glycine | 113.0 ± 0.000 | 100.5 ± 3.536 | 99.0 ± 4.243 | 86.0 ± 0.000 | 106.0 ± 0.000 |
| +5 mM TriSC + 1% HES | 106.0 ± 0.000 | 102.0 ± 1.414 | 99.0 ± 4.243 | 82.0 ± 0.000 | 98.0 ± 0.000 |
| +5 mM TriSC + 0.5% Glycine + 1% HES | 120.0 ± 0.000 | 101.0 ± 1.414 | 93.5 ± 10.607 | 80.0 ± 0.000 | 116.0 ± 0.000 |

TABLE 10

| Plasma Product | Pre-Lyo ATIII (%) | Post-Lyo ATIII (%) | 1 day at 40° C. ATIII (%) | 5 days at 40° C. ATIII (%) | 6 days at 40° C. ATIII (%) |
|---|---|---|---|---|---|
| Control | 85.0 ± 24.331 | 84.0 ± 14.731 | 77.3 ± 11.372 | 65.0 ± 4.243 | 71.5 ± 6.364 |
| +0.5% Glycine | 85.3 ± 23.288 | 84.7 ± 14.224 | 82.3 ± 13.650 | 67.0 ± 0.000 | 81.5 ± 9.192 |
| +1% HES | 87.0 ± 21.378 | 84.7 ± 14.364 | 78.0 ± 13.115 | 53.5 ± 10.607 | 74.0 ± 5.657 |
| +5 mM TriSodium Citrate | 84.0 ± 21.703 | 79.7 ± 10.017 | 77.0 ± 11.000 | 53.0 ± 8.485 | 72.0 ± 4.243 |
| +5 mM TriSC + 0.5% Glycine | 84.3 ± 20.551 | 83.3 ± 14.434 | 83.0 ± 12.767 | 58.5 ± 6.364 | 80.5 ± 12.021 |
| +5 mM TriSC + 1% HES | 84.3 ± 20.648 | 83.7 ± 12.423 | 79.7 ± 12.662 | 55.0 ± 7.071 | 69.5 ± 4.950 |
| +5 mM TriSC + 0.5% Glycine + 1% HES | 82.0 ± 20.881 | 83.0 ± 13.856 | 79.3 ± 15.275 | 59.0 ± 8.485 | 82.0 ± 16.971 |

TABLE 11

| Plasma Product | Pre-Lyo pH | Post-Lyo pH | 1 day at 40° C. pH | 5 days at 40° C. pH | 6 days at 40° C. pH |
|---|---|---|---|---|---|
| Control | 7.299 ± 0.076 | 7.943 ± 0.001 | Out of Range | Out of Range | Out of Range |
| +0.5% Glycine | 7.215 ± 0.177 | 7.831 ± 0.085 | 7.885 ± 0.087 | 7.909 ± 0.125 | 7.887 ± 0.110 |
| +1% HES | 7.388 ± 0.121 | Out of Range | Out of Range | Out of Range | Out of Range |
| +5 mM TriSodium Citrate | 7.270 ± 0.156 | 7.941 ± 0.016 | Out of Range | Out of Range | Out of Range |
| +5 mM TriSC + 0.5% Glycine | 7.258 ± 0.161 | 7.822 ± 0.087 | 7.884 ± 0.054 | 7.910 ± 0.081 | 7.934 ± 0.078 |
| +5 mM TriSC + 1% HES | 7.391 ± 0.139 | 7.902 ± 0.086 | 7.844 ± 0.000 | Out of Range | Out of Range |
| +5 mM TriSC + 0.5% Glycine + 1% HES | 7.370 ± 0.174 | 7.863 ± 0.071 | 7.9295 ± 0.049 | 7.920 ± 0.058 | 7.857 ± 0.000 |

TABLE 12

| Plasma Product | Pre-Lyo Osmolality (mOsm) | Post-Lyo Osmolality (mOsm) | 1 day at 40° C. Osmolality (mOsm) | 5 days at 40° C. Osmolality (mOsm) | 6 days at 40° C. Osmolality (mOsm) |
|---|---|---|---|---|---|
| Control | 291.0 ± 2.646 | 319.3 ± 54.721 | 280.0 ± 8.888 | 272.5 ± 7.778 | 272.0 ± 7.071 |
| +0.5% Glycine | 357.3 ± 1.528 | 347.0 ± 7.211 | 348.0 ± 5.568 | 338.5 ± 2.121 | 341.0 ± 1.414 |
| +1% HES | 296.0 ± 5.568 | 326.7 ± 45.938 | 291.3 ± 8.622 | 283.5 ± 7.778 | 281.0 ± 7.071 |
| +5 mM TriSodium Citrate | 303.7 ± 1.528 | 307.7 ± 8.145 | 306.7 ± 10.599 | 294.5 ± 6.364 | 295.0 ± 2.828 |
| +5 mM TriSC + 0.5% Glycine | 369.0 ± 1.000 | 372.0 ± 3.606 | 376.0 ± 13.077 | 363.5 ± 2.121 | 350.5 ± 19.092 |

TABLE 12-continued

| Plasma Product | Pre-Lyo Osmolality (mOsm) | Post-Lyo Osmolality (mOsm) | 1 day at 40° C. Osmolality (mOsm) | 5 days at 40° C. Osmolality (mOsm) | 6 days at 40° C. Osmolality (mOsm) |
|---|---|---|---|---|---|
| +5 mM TriSC + 1% HES | 307.7 ± 4.726 | 318.7 ± 13.503 | 325.3 ± 8.963 | 309.0 ± 14.142 | 303.5 ± 6.364 |
| +5 mM TriSC + 0.5% Glycine + 1% HES | 372.7 ± 3.786 | 374.3 ± 7.572 | 389.3 ± 5.508 | 372.5 ± 12.021 | 357.5 ± 26.163 |

TABLE 13

| Prothrombin Time (sec) | 100% Rehydration | 50% Rehydration | 100% Recovery |
|---|---|---|---|
| FFP Control | 16.340 ± 0.808 | 18.360 ± 1.610 | 16.980 ± 1.219 |
| FFP + Glycine + Citric Acid | 14.167 ± 0.683 | 14.400 ± 1.263 | 14.450 ± 0.896 |

TABLE 14

| Activated Partial Thromboplastin Time (sec) | 100% Rehydration | 50% Rehydration | 100% Recovery |
|---|---|---|---|
| FFP Control | 40.760 ± 5.763 | 50.960 ± 7.014 | 46.300 ± 7.407 |
| FFP + Glycine + Citric Acid | 36.500 ± 5.378 | 44.280 ± 3.885 | 38.300 ± 7.001 |

TABLE 15

| Thrombin Time (sec) | 100% Rehydration | 50% Rehydration | 100% Recovery |
|---|---|---|---|
| FFP Control | 18.933 ± 2.108 | 34.840 ± 1.494 | 21.233 ± 1.896 |
| FFP + Glycine + Critic Acid | 18.450 ± 0.373 | 26.467 ± 1.520 | 17.683 ± 0.264 |

TABLE 16

| Fibrinogen (mg/dL) | 100% Rehydration | 50% Rehydration | 100% Recovery |
|---|---|---|---|
| FFP Control | 208.200 ± 16.084 | 390.667 ± 8.505 | 215.000 ± 7.550 |
| FFP + Glycine + Critic Acid | 236.167 ± 36.755 | 437.000 ± 14.107 | 245.750 ± 36.124 |

TABLE 17

| Factor V Activity (%) | 100% Rehydration | 50% Rehydration | 100% Recovery |
|---|---|---|---|
| Control | 35.000 ± 8.860 | 45.500 ± 22.599 | 29.800 ± 9.149 |
| FFP + Glycine + Critic Acid | 57.833 ± 7.960 | 105.667 ± 26.741 | 56.333 ± 16.825 |

TABLE 18

| Factor VII Activity (%) | 100% Rehydration | 50% Rehydration | 100% Recovery |
|---|---|---|---|
| Control | 83.200 ± 20.462 | 132.800 ± 24.682 | 76.000 ± 21.373 |
| FFP + Glycine + Critic Acid | 87.667 ± 16.071 | 140.800 ± 25.528 | 82.167 ± 23.095 |

TABLE 19

| Factor VIII Activity (%) | 100% Rehydration | 50% Rehydration | 100% Recovery |
|---|---|---|---|
| Control | 54.333 ± 3.786 | 74.334 ± 18.717 | 42.000 ± 12.767 |
| FFP + Glycine + Critic Acid | 81.667 ± 5.132 | 125.333 ± 11.846 | 74.334 ± 10.970 |

TABLE 20

| Factor IX Activity (%) | 100% Rehydration | 50% Rehydration | 100% Recovery |
|---|---|---|---|
| Control | 71.000 ± 17.132 | 125.800 ± 35.731 | 71.200 ± 25.233 |
| FFP + Glycine + Critic Acid | 74.000 ± 16.480 | 126.500 ± 35.237 | 83.200 ± 28.595 |

TABLE 21

| Factor X Activity (%) | 100% Rehydration | 50% Rehydration | 100% Recovery |
|---|---|---|---|
| Control | 67.400 ± 15.110 | 133.400 ± 39.278 | 59.600 ± 21.208 |
| FFP + Glycine + Critic Acid | 73.000 ± 17.709 | 148.800 ± 42.086 | 65.400 ± 21.007 |

TABLE 22

| Protein S (%) | 100% Rehydration | 50% Rehydration | 100% Recovery |
|---|---|---|---|
| Control | 60.5 ± 5.536 | 122.333 ± 39.808 | 59.500 ± 4.950 |
| FFP + Glycine + Critic Acid | 63.500 ± 3.536 | 113.000 ± 46.329 | 59.000 ± 14.142 |

TABLE 23

| Protein C (%) | 100% Rehydration | 50% Rehydration | 100% Recovery |
|---|---|---|---|
| Control | 80.600 ± 7.436 | 150.833 ± 38.285 | 80.800 ± 15.991 |
| FFP + Glycine + Critic Acid | 84.833 ± 14.428 | 149.333 ± 37.798 | 81.000 ± 9.798 |

TABLE 24

| Anti Thrombin III (%) | 100% Rehydration | 50% Rehydration | 100% Recovery |
|---|---|---|---|
| Control | 81.200 ± 16.115 | 176.334 ± 40.352 | 84.834 ± 16.845 |
| FFP + Glycine + Critic Acid | 87.667 ± 17.829 | 178.334 ± 43.019 | 87.334 ± 16.681 |

TABLE 25

| pH | 100% Rehydration | 50% Rehydration | 100% Recovery |
|---|---|---|---|
| Control | 7.881 ± 0.163 | 7.839 ± 0.223 | Out of Range |
| FFP + Glycine + Critic Acid | 7.411 ± 0.324 | 7.421 ± 0.354 | 7.520 ± 0.349 |

TABLE 26

| Osmolality | 100% Rehydration | 50% Rehydration | 100% Recovery |
|---|---|---|---|
| Control | 289.000 ± 8.390 | 561.429 ± 12.231 | 271.143 ± 10.007 |
| FFP + Glycine + Critic Acid | 351.286 ± 11.800 | 685.143 ± 13.359 | 328.857 ± 12.348 |

TABLE 27

| Plasma Product | Pre-Lyo PT (sec) | Post-Lyo PT (sec) | 4 days at 40° C. PT (sec) | 5 days at 40° C. PT (sec) | 6 days at 40° C. PT (sec) |
|---|---|---|---|---|---|
| Control | 14.5 ± 1.202 | 14.4 ± 0.000 | 18.7 ± 1.061 | 18.6 ± 0.354 | 19.4 ± 0.566 |
| +8 mM $NH_4SO_4$ | 13.7 ± 0.354 | 14.2 ± 0.636 | 15.6 ± 0.354 | 16.1 ± 0.566 | 16.3 ± 0.495 |
| +6 mM $NH_4SO_4$ | 13.7 ± 0.283 | 14.2 ± 0.424 | 16.0 ± 0.354 | 16.1 ± 0.354 | 16.4 ± 0.354 |
| +3 mM $NH_4SO_4$ | 13.6 ± 0.212 | 14.4 ± 0.424 | 16.9 ± 0.990 | 17.2 ± 0.495 | 17.5 ± 0.990 |
| +1.5 mM $NH_4SO_4$ | 13.5 ± 0.212 | 14.2 ± 0.141 | 17.6 ± 0.495 | 18.0 ± 0.919 | 18.4 ± 1.273 |

TABLE 28

| Plasma Product | Pre-Lyo aPPT (sec) | Post-Lyo aPPT (sec) | 4 days at 40° C. aPPT (sec) | 5 days at 40° C. aPPT (sec) | 6 days at 40° C. aPPT (sec) |
|---|---|---|---|---|---|
| Control | 31.2 ± 2.687 | 34.15 ± 4.313 | 43.8 ± 6.364 | 43.35 ± 5.586 | 44.6 ± 8.202 |
| +8 mM NH$_4$SO$_4$ | 31.65 ± 1.202 | 32.95 ± 3.465 | 37.5 ± 4.808 | 38.6 ± 5.940 | 39.3 ± 5.303 |
| +6 mM NH$_4$SO$_4$ | 31.65 ± 1.344 | 33.15 ± 3.748 | 38.95 ± 5.728 | 38.8 ± 5.091 | 40.2 ± 4.172 |
| +3 mM NH$_4$SO$_4$ | 31.25 ± 2.616 | 33.65 ± 3.465 | 40.0 ± 6.788 | 40.9 ± 5.233 | 42.4 ± 6.152 |
| +1.5 mM NH$_4$SO$_4$ | 31.2 ± 3.111 | 34.35 ± 3.323 | 40.95 ± 5.303 | 42.75 ± 6.435 | 44.0 ± 7.071 |

TABLE 29

| Plasma Product | Pre-Lyo TT (sec) | Post-Lyo TT (sec) | 4 days at 40° C. TT (sec) | 5 days at 40° C. TT (sec) | 6 days at 40° C. TT (sec) |
|---|---|---|---|---|---|
| Control | 19.1 ± 0.990 | 19.2 ± 0.707 | 25.8 ± 3.818 | 27.2 ± 3.960 | 28.8 ± 2.687 |
| +8 mM NH$_4$SO$_4$ | 20.4 ± 0.990 | 19.9 ± 0.707 | 23.1 ± 3.253 | 23.9 ± 4.101 | 24.5 ± 3.323 |
| +6 mM NH$_4$SO$_4$ | 19.8 ± 0.707 | 19.5 ± 0.919 | 23.0 ± 3.465 | 24.0 ± 5.020 | 24.8 ± 3.536 |
| +3 mM NH$_4$SO$_4$ | 19.3 ± 0.990 | 19.3 ± 1.344 | 24.4 ± 3.182 | 25.9 ± 4.455 | 26.7 ± 3.536 |
| +1.5 mM NH$_4$SO$_4$ | 18.8 ± 0.707 | 19.5 ± 1.344 | 25.4 ± 3.041 | 26.8 ± 5.586 | 28.1 ± 3.889 |

TABLE 30

| Plasma Product | Pre-Lyo FIB (mg/dL) | Post-Lyo FIB (mg/dL) | 4 days at 40° C. FIB (mg/dL) | 5 days at 40° C. FIB (mg/dL) | 6 days at 40° C. FIB (mg/dL) |
|---|---|---|---|---|---|
| Control | 194.5 ± 53.033 | 196.0 ± 49.497 | 185.5 ± 40.305 | 179.5 ± 43.134 | 172.5 ± 37.477 |
| +8 mM NH$_4$SO$_4$ | 196.0 ± 46.669 | 194.5 ± 41.719 | 187.5 ± 38.891 | 180.5 ± 38.891 | 177.5 ± 38.891 |
| +6 mM NH$_4$SO$_4$ | 192.5 ± 50.205 | 189.5 ± 48.790 | 184.5 ± 40.305 | 181.0 ± 50.912 | 178.0 ± 41.012 |
| +3 mM NH$_4$SO$_4$ | 194.5 ± 47.376 | 190.5 ± 62.933 | 176.0 ± 41.012 | 184.0 ± 55.154 | 178.0 ± 38.184 |
| +1.5 mM NH$_4$SO$_4$ | 199.5 ± 48.790 | 191.5 ± 53.033 | 181.0 ± 43.841 | 178.0 ± 53.740 | 179.0 ± 38.184 |

TABLE 31

| Plasma Product | Pre-Lyo Factor V (%) | Post-Lyo Factor V (%) | 4 days at 40° C. Factor V (%) | 5 days at 40° C. Factor V (%) | 6 days at 40° C. Factor V (%) |
|---|---|---|---|---|---|
| Control | 78.5 ± 17.678 | 71.0 ± 0.000 | 27.0 ± 4.243 | 37.5 ± 2.121 | 37.0 ± 1.414 |
| +8 mM NH$_4$SO$_4$ | 69.5 ± 21.920 | 74.5 ± 0.707 | 55.5 ± 2.121 | 55.0 ± 7.071 | 53.5 ± 2.121 |
| +6 mM NH$_4$SO$_4$ | 75.5 ± 12.021 | 73.5 ± 2.121 | 50.0 ± 4.243 | 55.0 ± 2.828 | 54.0 ± 0.000 |
| +3 mM NH$_4$SO$_4$ | 68.0 ± 19.799 | 70.5 ± 2.121 | 41.0 ± 4.243 | 43.5 ± 0.707 | 46.0 ± 0.000 |
| +1.5 mM NH$_4$SO$_4$ | 82.0 ± 4.243 | 70.5 ± 3.536 | 35.0 ± 4.243 | 39.0 ± 1.414 | 42.5 ± 0.707 |

TABLE 32

| Plasma Product | Pre-Lyo Factor VIII (%) | Post-Lyo Factor VIII (%) | 4 days at 40° C. Factor VIII (%) | 5 days at 40° C. Factor VIII (%) | 6 days at 40° C. Factor VIII (%) |
|---|---|---|---|---|---|
| Control | 126.0 ± 55.154 | 83.5 ± 51.619 | 69.5 ± 53.033 | 93.5 ± 71.418 | 62.0 ± 32.527 |
| +8 mM NH$_4$SO$_4$ | 119.0 ± 55.154 | 156.0 ± 128.693 | 116.5 ± 98.288 | 157.5 ± 133.643 | 87.0 ± 45.255 |
| +6 mM NH$_4$SO$_4$ | 104.0 ± 29.698 | 147.0 ± 118.794 | 108.5 ± 95.459 | 148.0 ± 117.380 | 87.0 ± 42.426 |

TABLE 32-continued

| Plasma Product | Pre-Lyo Factor VIII (%) | Post-Lyo Factor VIII (%) | 4 days at 40° C. Factor VIII (%) | 5 days at 40° C. Factor VIII (%) | 6 days at 40° C. Factor VIII (%) |
|---|---|---|---|---|---|
| +3 mM NH$_4$SO$_4$ | 98.5 ± 28.991 | 137.0 ± 108.894 | 86.5 ± 71.418 | 126.0 ± 100.409 | 76.0 ± 38.184 |
| +1.5 mM NH$_4$SO$_4$ | 103.5 ± 36.062 | 129.0 ± 106.066 | 75.5 ± 55.861 | 109.0 ± 87.681 | 67.5 ± 33.234 |

The invention claimed is:

1. A method for preparing a freeze-dried plasma product comprising:
adding glycine under sterile conditions to sterile, pathogen-free plasma to form a mixture of glycine and the sterile, pathogen-free plasma,
freezing and drying the mixture under conditions that suppress recrystallization of glycine to form a freeze-dried product,
storing the freeze-dried product.

2. The method of claim 1 further comprising:
freezing the mixture by:
loading the mixture at room temperature into a freezable container;
placing the freezable container into a lyophilizer;
freezing the mixture to −4° C. at 2° C. per minute;
holding the temperature for 10 minutes;
freezing the mixture to −40° C. at 1° C. per minute; and
holding the temperature for 120 minutes.

3. The method of claim 2 further comprising:
drying the mixture by:
setting the lyophilizer chamber pressure to 0.6 mbar;
increasing the temperature to 20° C. at 0.2° C. per minute;
holding for 10 hour;
reducing the chamber pressure to 0.0 mbar; and
holding the temperature at 20° C. for 7 hour.

* * * * *